US007164012B2

(12) United States Patent
Hunter et al.

(10) Patent No.: US 7,164,012 B2
(45) Date of Patent: *Jan. 16, 2007

(54) NIMA INTERACTING PROTEINS

(75) Inventors: Tony Hunter, Del Mar, CA (US); Kun Ping Lu, Newton, MA (US)

(73) Assignee: The Salk Institue for Biological Studies, La Jolla, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 10/616,410

(22) Filed: Jul. 8, 2003

(65) Prior Publication Data

US 2005/0033032 A1     Feb. 10, 2005

Related U.S. Application Data

(60) Continuation of application No. 09/275,900, filed on Mar. 24, 1999, now Pat. No. 6,596,848, which is a division of application No. 09/066,074, filed on Apr. 24, 1998, now Pat. No. 5,952,467, which is a division of application No. 08/555,912, filed on Nov. 13, 1995, now Pat. No. 5,972,697.

(51) Int. Cl.
C07H 21/02 (2006.01)
C12P 21/06 (2006.01)

(52) U.S. Cl. .................................. 536/23.1; 435/69.1
(58) Field of Classification Search ................ 536/23.1
See application file for complete search history.

(56) References Cited

U.S. PATENT DOCUMENTS

| | | | |
|---|---|---|---|
| 5,443,962 A | 8/1995 | Draetta et al. | |
| 5,952,467 A | 9/1999 | Hunter et al. | |
| 6,596,848 B1 | 7/2003 | Hunter et al. | |
| 2002/0025521 A1 | 2/2002 | Lu et al. | |
| 2003/0225528 A1* | 12/2003 | Baker et al. | 702/19 |
| 2004/0101896 A1 | 5/2004 | Hunter et al. | |
| 2004/0171019 A1* | 9/2004 | Matthews et al. | 435/6 |
| 2005/0027107 A1 | 2/2005 | Hunter et al. | |
| 2005/0049404 A1 | 3/2005 | Hunter et al. | |

FOREIGN PATENT DOCUMENTS

| | | |
|---|---|---|
| WO | WO 99/12962 | 3/1999 |
| WO | WO 00/48621 | 8/2000 |
| WO | WO 01/75067 | 10/2001 |
| WO | WO 01/79449 | 10/2001 |

OTHER PUBLICATIONS

Mathews and Van Holde, Biochemistry, 1996, pp. 165-171.*
Burgess et al, Possible Dissociation of the Heparin-binding and Mitogenic Activities of Heparin-binding (Acidic Fibroblast) Growth Factor-1 from Its Receptor-binding Activities by Site-directed MutagenesisJournal of Cell biology, vol. 111, p. 2129-2138, 1990.*
Orkin et al., Report and Recommendation of the Panel to Assess the NIH Investment in Research on Gene Therapy, NIH, 1995.*
Eck et al., (Gene-Based Therapy, In: The Pharmacological Basis ofTherapeutics, Goodman and Gilman, Ed.s, 1996, pp. 77-101.*
Verma I and Somia N, Nature, 1997, vol. 389, pp. 239-242.*
Amon et al., "Regulation of p34$^{CDC28}$ tyrosine phosphorylation is not required for entry into mitosis in S. cerevisiae." Nature, 355:368-371, 1992.
Burgess et al., "Possible dissociation of the heparin-binding and mitogenic activities of heparin-binding (acidic fibroblast) growth factor-1 from its receptor-binding activities by site-directed mutagenesis of a single lysine residue." J. Cell Biol., 111:2129-2138, 1990.
Cech, "Ribozymes and Their Medical Implications." J. Am. Med. Assn., 260(20):3030-3034, 1988.
Choi et al., "Activation of p34$^{cdc2}$ protein kinase activity in meiotic and mitotic cell cycles in mouse oocytes and embryos." Development, 113:789-795, 1991.
Chong et al., "A human telomeric protein." Science, 270:1663-1667, 1995.
Durfee et al., "The retinoblastoma protein associates with the protein phosphatase type 1 catalytic subunit." Genes Dev., 7:555-569, 1993.
Dyck et al., "A Novel Macromolecular Structure Is a Target of the Promyelocyte-Retinoic Acid Receptor Oncoprotein." Cell, 76:333-343, 1994.
Eldredge et al., "Use of Tetracycline Operator System to Regulate Oncogene Expression in Mammalian Cells." Methods Enzymol., 254:481-491, 1995.
Engleman, Human Hydbridomas and Monoclonal Antibodies, New York:Plenum Press, 1985.
Fields and Song, "A novel genetic system to detect protein—protein interactions." Nature, 340:245-246, 1989.
Fraley and Papahadjopoulos, "New generation lipsomes: the engineering of an efficient vehicle for intracellular delivery of nucleic acids." Trends Biochem. Sci., 6:77-80, 1981.
Fruman et al., "Immunophilins in protein folding and immunosuppression." FASEB J., 8:391-400, 1994.
Fu and Maniatis, "Factor required for mammalian spliceosome assembly is localized to discrete regions in the nucleus." Nature, 343:437-441, 1990.
Fujimori et al., "Mice Lacking Pin1 Develop Normally, but Are Defective in Entering Cell Cycle from $G_0$ Arrest." Biochem. Biophys. Res. Commun., 265:658-663, 1999.
Gavin et al., "Histone H1 kinase activity, germinal vesicle breakdown and M phase entry in mouse oocytes." J. Cell Sci., 107:275-283, 1994.

(Continued)

Primary Examiner—Jeffrey Siew
Assistant Examiner—Lei Yao
(74) Attorney, Agent, or Firm—Klarquist Sparkman, LLP

(57) ABSTRACT

A novel class of NIMA interacting proteins (PIN), exemplified by Pin1, is provided. Pin1 induces a G2 arrest and delays NIMA-induced mitosis when overexpressed, and triggers mitotic arrest and DNA fragmentation when depleted. Methods of identifying other Pin proteins and Pin-interacting proteins and identifying compositions which affect Pin activity or expression are also provided.

9 Claims, 10 Drawing Sheets

OTHER PUBLICATIONS

Gossen and Bujard, "Tight control of gene expression in mammalian cells by tetracycline-responsive promoters." *Proc. Natl. Acad. Sci. USA*, 89:5547-5551, 1992.

Gui et al., "A serine kinase regulates intracellular localization of splicing factors in the cell cycle." *Nature*, 369:678-682, 1994.

Hanes et al., "Sequence and Mutational Analysis of *ESS1*, a Gene Essential for Growth in *Saccharomyces cerevisiae*." *Yeast*, 5:55-72, 1989.

Hani et al., "*PTF1* encodes an essential protein in *Saccharomyces cerevisiae*, which shows strong homology with a new putative family of PPIases." *FEBS Lett.*, 365:198-202, 1995.

Hannon et al., "Isolation of the Rb-related p130 through its interaction with CDK2 and cyclins." *Genes Dev.*, 7:2378-2391, 1993.

Harper et al., "The p21 Cdk-Interacting Protein Cip1 Is a Potent Inhibitor of G1 Cyclin-Dependent Kinases." *Cell*, 75:805-816, 1993.

Heitman et al., "Identification of Immunosuppressive Drug Targets in Yeast." *Methods Companion Methods Enzymol.*, 5:176-187, 1993.

Helene, "The anti-gene strategy: control of gene expression by triplex-forming-oligonucleotides." *Anticancer Drug Des.*, 6:569-584, 1991 (abstract only).

Hillier et al., EST-STS Database, Accession No. H41102, 1991.

Hillier et al., EST-STS Database, Accession No. T82035, 1995.

Jaye et al., "Isolation of a human anti-haemophilic factor IX cDNA clone using a unique 52-base synthetic oligonucleotide probe deduced from the amino acid sequence of bovine factor IX." *Nucl. Acid Res.*, 11(8):2325-2335, 1983.

Jung et al., "Kinetics of MPF and histone H1 kinase activity differ during the G2- to M-phase transition in mouse oocytes." *Int. J. Dev. Biol.*, 37:595-600, 1993.

Kohler and Milstein, "Continuous cultures of fused cells secreting antibody of predefined specificity." *Nature*, 256:495-497, 1975.

Lambert-Messerlian et al., "Human follicular fluid contains pro- and C-terminal immunoreactive alpha-inhibin precursor proteins." *J. Clin. Endocrinol. Metab.*, 78:433-439, 1994.

Lazar et al., "Transforming growth factor alpha: mutation of aspartic acid 47 and leucine 48 results in different biological activities." *Mol. Cell Biol.*, 8:1247-1252, 1988.

Lee and Nathans, "Proliferin Secreted by Cultured Cells Binds to Mannose 6-Phosphase Receptors." *J. Biol. Chem.*, 263(7):3521-3527, 1988.

Lu et al., "Properties and regulation of the cell cycle-specific NIMA protein kinase of *Aspergillus nidulans*." *J. Biol. Chem.*, 268:8769-8776, 1993.

Lu et al., "Identification of Substrate Specificity Determinants for the Cell Cycle-regulated NIMA Protein Kinase." *J. Biol. Chem.*, 269:6603-6607, 1994.

Lu et al., "Evidence for a NIMA-like mitotic pathway in vertebrate cells." *Cell*, 81:413-424, 1995.

Lu et al., "Expression of the noncatalytic domain of the NIMA kinase causes a G2 arrest in *Aspergillus nidulans*." *EMBO J.*, 13:2103-2113, 1994.

Lu et al., "A human peptidyl-prolyl isomerase essential for regulation of mitosis." *Nature*, 380:544-547, 1996.

Maher et al., "Oligonucleotide-Directed DNA Triple-Helix Formation: An Approach to Artificial Repressors?" *Antisense Res. Dev.*, 1:277-281, 1991.

Mannino and Gould-Fogerite, "Liposome Mediated Gene Transfer." *Biotechniques*, 6(7):682-690, 1988.

Marcus-Sekura, "Review: Techniques for Using Antisense Oligodeoxyribonucleotides to Study Gene Expression." *Anal. Biochem.*, 172:289-295, 1988.

Morris et al., "The genetic analysis of mitosis in *Aspergillus nidulans*." *Bioessays*, 10:196-201, 1989.

O'Connell et al., "Premature chromatin condensation upon accumulation of NIMA." *EMBO J.*, 13:4926-4937, 1994.

Osmani et al., "Mitotic induction and maintenance by overexpression of a G2-specific gene that encodes a potential protein kinase." *Cell*, 53:237-244, 1988.

Osmani et al., "Parallel Activation of the NIMA and $p34^{cdc2}$ Cell Cycle-Regulated Protein Kinases Is Required to Initiate Mitosis in *A. nidulans*." *Cell*, 67:283-291, 1991.

Peattie et al., "Expression and characterization of human FKBP52, an immunophilin that associates with the 90-kDa heat shock protein and is a component of steroid receptor complexes." *Proc. Natl. Acad. Sci. USA*, 89:10974-10979, 1992.

Rahfeld et al., "Confirmation of the existence of a third family among peptidyl-prolyl cis/trans isomerases: Amino acid sequence and recombinant production of parvulin." *FEBS Lett.*, 352:180-184, 1994.

Rosborough et al., "Identification of FKBP-related proteins with antibodies of predetermined specificity and isolation by FK 506 affinity chromatography." *Transplantation Proc.*, 23:2890-2893, 1991.

Rosenberg et al., "Vectors for selective expression of cloned DNAs by T7 RNA polymerase." *Gene*, 56:125-135, 1987.

Rudd et al., "A new family of peptidyl-prolyl isomerases." *Trends Biochem. Sci.*, 20:12-14, 1995.

Sazer et al., "Mitochondrial growth and DNA synthesis occur in the absence of nuclear DNA replication in fission yeast." *J. Cell Sci.*, 97:509-516, 1990.

Schreiber, "Chemistry and Biology of the Immunophilins and Their Immunosuppressive Ligands." *Science*, 251:283-287, 1991.

Schultz et al., "Cell Cycle-dependent Expression of Nek2, a Novel Human Protein Kinase Related to the NIMA Mitotic Regulator of *Asperigillus nidulans*[1]." *Cell. Growth Differ.*, 5:625-635, 1994.

Schultz et al., "Identification of 21 Novel Human Protein Kinases, Including 3 Members of a Family Related to the Cell Cycle Regulator *nimA* of *Aspergillus nidulans*[1]." *Cell Growth Differ.*, 4:821-830, 1993.

Schweitzer et al., "*NPK1*, a nonessential protein kinase gene in *Saccharomyces cerevisiae* with similarity to *Aspergillus nidulans nimA*." *Mol. Gen. Genet.*, 234:164-167, 1992.

Sikorski and Hieter, "A System of Shuttle Vectors and Yeast Host Strains Designed for Efficient Manipulation of DNA in *Saccharomyces cerevisiae*." *Genetics*, 122:19-27, 1989.

Sorger and Murray, "S-phase feedback control in budding yeast independent of tyrosine phosphorylation of $p34^{cdc28}$." *Nature*, 355:365-368, 1992.

Stueland et al., "Full Activiation of $p34^{CDC28}$ Histone H1 Kinase Activity Is Unable To Promote Entry into Mitosis in checkpoint-Arrested Cells of the Yeast *Saccharomyces cerevisiae*." *Mol. Cell. Bio.*, 13:3744-3755, 1993.

Sudol et al., "Characterization of a novel protein-binding module—the WW domain." *FEBS Lett.*, 369:67-71, 1995.

Sudol et al., "Characterization of the Mammalian YAP (Yes-associated Protein) Gene and Its Role in Defining a Novel Protein Module, the WW Domain." *J. Biol. Chem.*, 270(24):14733-14741, 1995.

Wallace et al., "The use of synthetic oligonucleotides as hybridization probes. II. Hybridization of oligonucleotides of mixed sequence to rabbit β-globin DNA." *Nucl. Acid Res.*, 9(4):879-894, 1981.

Weintraub, "Antisence RNA and DNA." *Scientific American*, 262:40-46, 1990.

Yocum et al., "Use of *lac* Z fusions to Delimit Regulatory Elements of the Inducible Divergent *GAL1- GAL10* Promoter in *Saccharomyces cerevisiae*." *Mol. Cell. Bio.*, 4(10):1985-1998, 1984.

Yoon et al., "Genetic and Biochemical Interactions between an Essential Kinetochore Protein, Cbf2p/Ndc10p, and the *CDC34* Ubiquitin-Conjugating Enzyme." *Mol. Cell. Biol.*, 15:4835-4842, 1995.

\* cited by examiner

| pAS2 Insert | Colony Color | | |
|---|---|---|---|
| | pGAD GH Insert | | |
| | PIN1 | PIN2 | PIN3 |
| NIMA | Blue | Blue | Blue |
| K40M NIMA | Blue | Blue | Blue |
| NIMA280-699 | Blue | Blue | White |
| NLK1 | White | White | Blue |
| NIMA280-699FS | White | White | White |

TGCTGGCCAGCACCTCGAGGGAAG

```
  1 ATGGCGGACGAGGAGAAGCTGCCGCCCGGCTGGGAGAAGCGCATGAGCCGCAGCTCAGGC
    M  A  D  E  E  K  L  P  P  G  W  E  K  R  M  S  R  S  S  G     20

61 CGAGTGTACTACTTCAACCACATCACTAACGCCAGCCAGTGGGAGCGGCCCAGCGGCAAC
    R  V  Y  Y  F  N  H  I  T  N  A  S  Q  W  E  R  P  S  G  N     40

121 AGCAGCAGTGGTGGCAAAAACGGGCAGGGGGAGCCTGCCAGGGTCCGCTGCTCGCACCTG
    S  S  S  G  G  K  N  G  Q  G  E  P  A  R  V  R  C  S  H  L     60

181 CTGGTGAAGCACAGCCAGTCACGGCGGCCCTCGTCCTGGCGGCAGGAGAAGATCACCCGG
    L  V  K  H  S  Q  S  R  R  P  S  S  W  R  Q  E  K  I  T  R     80

241 ACCAAGGAGGAGGCCCTGGAGCTGATCAACGGCTACATCCAGAAGATCAAGTCGGGAGAG
    T  K  E  E  A  L  E  L  I  N  G  Y  I  Q  K  I  K  S  G  E    100

301 GAGGACTTTGAGTCTCTGGCCTCACAGTTCAGCGACTGCAGCTCAGCCAAGGCCAGGGGA
    E  D  F  E  S  L  A  S  Q  F  S  D  C  S  S  A  K  A  R  G    120

361 GACCTGGGTGCCTTCAGCAGAGGTCAGATGCAGAAGCCATTTGAAGACGCCTCGTTTGCG
    D  L  G  A  F  S  R  G  Q  M  Q  K  P  F  E  D  A  S  F  A    140

421 CTGCGGACGGGGGAGATGAGCGGGCCCGTGTTCACGGATTCCGGCATCCACATCATCCTC
    L  R  T  G  E  M  S  G  P  V  F  T  D  S  G  I  H  I  I  L    160

481 CGCACTGAGTGAGGGTGGGGAGCCCAGGCCTGGCCTCGGGGCAGGGCAGGGCGGCTAGGC
    R  T  E  *

541 CGGCCAGCTCCCCCTTGCCCGCCAGCCAGTGGCCGAACCCCCCACTCCCTGCCACCGTCA
601 CACAGTATTTATTGTTCCCACAATGGCTGGGAGGGGGCCCTTCCAGATTGGGGGCCCTGG
661 GGTCCCCACTCCCTGTCCATCCCCAGTTGGGGCTGCGACCGCCAGATTCTCCCTTAAGGA
721 ATTGACTTCAGCAGGGGTGGGAGGCTCCCAGACCCAGGGCAGTGTGGTGGGAGGGGTGTT
781 CCAAAGAGAAGGCCTGGTCAGCAGAGCCGCCCCGTGTCCCCCCAGGTGCTGGAGGCAGAC
841 TCGAGGGCCGAATTGTTTCTAGTTAGGCCACGCTCCTCTGTTCAGTCGCAAAGGTGAACA
901 CTCATGCGGCAGCCATGGGCCCTCTGAGCAACTGTGCAGACCCTTTCACCCCCAATTAAA
961 CCCAGAACCACTAAAAAAAAAAAAAAAAAA
```

| | | | | | | | | | | | | | | | | | | | | | | | |
|---|---|---|---|---|---|---|---|---|---|---|---|---|---|---|---|---|---|---|---|---|---|---|---|
| Pin1/Human | 5 | E K L P P G W E K R M S S G R V Y Y F N H I T N A S Q W E R P S G N S S S |
| Ess1/SC | 9 | T G L P T P W T V R Y S K S K K R E Y F F N P E T K H T T W Q D D P R K A M L S |
| Yap/Human | 171 | V P L P A G W E M A K T D R S - G Q R Y F L N H I D Q T T T W Q D P R K A M L S |
| Nedd4/Mouse | ? | S P L P P G W E E R Q D D V L - G R T Y Y V N H E S R R T T T W K R P T L D Q T E |
| RSP5/SC | 228 | G R L P P G W E R R T D N F - G R T Y Y V D H N T R T T Q W E R P T P Q G R P - |
| Drd/Human | 3052 | T S V Q G P W E R R A I S P N K V P - Y Y I H H E T Q T T C W D H P K M T E L Y |
| FE65/Rat | 12 | S D L P A G W M R V Q D T S - G - T Y Y W H I P T G T T Q W E P P G R A S P S |
| Consensus | | . . L P . G W E . . . . . . . G . Y Y . N H . T . T . T . W . . . . P . . . . |

FIG. 2C

| | | | | | | | | | | | | | | | | | | | | | | | |
|---|---|---|---|---|---|---|---|---|---|---|---|---|---|---|---|---|---|---|---|---|---|---|---|
| Pin1/Human | 59 | H L L V K H S Q S R R P S S W R Q E K I T R T K E E A L E L I N G Y I Q K I K |
| Ess1/SC | 63 | H I L I K H H - - - - - - - - - S S S K H R S S E N I T I S - - K E E A T D E L K T L I T R L D |
| Parvulin/EC | 8 | H I L V - - - - - - - - - - - - - - - - - - - - - - - - E E K L A L - - D L L E Q I K |
| PrsA/BS | 140 | H I L V A D K K T - - - - - - - - - - - - - - - - - - - A E E V E K - - I - K L K |
| Cbf2/CJ | 137 | H I L V A T - - - - - - - - - - - - - - - - - - - - - E K E A K D I H N E L K G L K |
| EST/AT | ? | | | | | | | | | | | | | | | E | | | | | | | | | | H I K |
| Consensus | | H I L V . . . . . . . . . . . . . . . . . . . . . . . . . . . . . . . K |

| | | | | | | | | | | | | | | | | | | | | | | | | |
|---|---|---|---|---|---|---|---|---|---|---|---|---|---|---|---|---|---|---|---|---|---|---|---|---|
| | | S G E - - E D F F E E S L A S Q F S D D C S A K A - R G D L G A F S R - G Q M Q K | | | | | | | | | | | | | | | | | | | | | | |
| | | D D S K T N S F - E A L A K K E R S H S I C P S G G D D L G W F G R - G E M Q P | | | | | | | | | | | | | | | | | | | | | | |
| | | N G - - I K - A D F G K L A K K H S I T D S G G D L G W F E F - R Q G Q M V P | | | | | | | | | | | | | | | | | | | | | | |
| | | K G E K - - F E D L A K F S E L A K E Y S I D P G S K N Q - G G D L G W F A K E - G Q M D E | | | | | | | | | | | | | | | | | | | | | | |
| | | G K E L D A K F - A N F E E V A T R V S D C S S A K R - G G D L G S F G R - D Q S T M V K | | | | | | | | | | | | | | | | | | | | | | |
| | | V S K - - - - - - - - - - - - - L A K - - . - - . - C S S . K . G G D L G . F . R . G Q M Q K | | | | | | | | | | | | | | | | | | | | | | |

| | | | | | | | | | | | | | | | | | | | | | | | | |
|---|---|---|---|---|---|---|---|---|---|---|---|---|---|---|---|---|---|---|---|---|---|---|---|---|
| Pin1/Human | 164 | P F E D A S F A L R T G E M S G - P V F T D S G I H I I L R T E . Q M Q K . |
| Ess1/SC | 170 | S F E D A A F Q L K V G E E V S D - I V E S G S G V H V I I K R V G . H I K . |
| Parvulin/EC | 93 | A F D K V V F S C P V L E P T G - P L H T Q F G Y H I K K T E . Q I K . |
| PrsA/BS | 215 | T F S K A A F A L K N G T I T T P - P V K K T N F G Y H V I L K E N . K L K . |
| Cbf2/CJ | 219 | P F T D A A F T Y A L K V G D I S D - I V D T D S G V H I I K R T E . G L K . |
| EST/AT | 69 | P F E E A T Y A L K V G D I S D - . . . . . G Y H I I K . . . . |
| Consensus | | . F . D A A F . L K . G E . S . . . P V . T . . G Y H I I K . . . . . . |

SEQUENCE LISTING

<160> NUMBER OF SEQ ID NOS: 22

<210> SEQ ID NO 1
<211> LENGTH: 1014
<212> TYPE: DNA
<213> ORGANISM: Homo sapiens

```
<220> FEATURE:
<221> NAME/KEY: CDS
<222> LOCATION: (25)...(513)

<400> SEQUENCE: 1
tgctggccag cacctcgagg gaag atg gcg gac gag gag aag ctg ccg ccc        51
                          Met Ala Asp Glu Glu Lys Leu Pro Pro
                            1               5 ggc tgg gag aag cgc atg agc cgc agc tca ggc cga gtg tac tac ttc       99
Gly Trp Glu Lys Arg Met Ser Arg Ser Ser Gly Arg Val Tyr Tyr Phe
 10                  15                  20                  25 aac cac atc act aac gcc agc cag tgg gag cgg ccc agc ggc aac agc      147
Asn His Ile Thr Asn Ala Ser Gln Trp Glu Arg Pro Ser Gly Asn Ser
                 30                  35                  40 agc agt ggt ggc aaa aac ggg cag ggg gag cct gcc agg gtc cgc tgc      195
Ser Ser Gly Gly Lys Asn Gly Gln Gly Glu Pro Ala Arg Val Arg Cys
             45                  50                  55 tcg cac ctg ctg gtg aag cac agc cag tca cgg cgg ccc tcg tcc tgg      243
Ser His Leu Leu Val Lys His Ser Gln Ser Arg Arg Pro Ser Ser Trp
         60                  65                  70 cgg cag gag aag atc acc cgg acc aag gag gag gcc ctg gag ctg atc      291
Arg Gln Glu Lys Ile Thr Arg Thr Lys Glu Glu Ala Leu Glu Leu Ile
     75                  80                  85 aac ggc tac atc cag aag atc aag tcg gga gag gag gac ttt gag tct      339
Asn Gly Tyr Ile Gln Lys Ile Lys Ser Gly Glu Glu Asp Phe Glu Ser
 90                  95                 100                 105 ctg gcc tca cag ttc agc gac tgc agc tca gcc aag gcc agg gga gac      387
Leu Ala Ser Gln Phe Ser Asp Cys Ser Ser Ala Lys Ala Arg Gly Asp
                110                 115                 120 ctg ggt gcc ttc agc aga ggt cag atg cag aag cca ttt gaa gac gcc      435
Leu Gly Ala Phe Ser Arg Gly Gln Met Gln Lys Pro Phe Glu Asp Ala
            125                 130                 135 tcg ttt gcg ctg cgg acg ggg gag atg agc ggg ccc gtg ttc acg gat      483
Ser Phe Ala Leu Arg Thr Gly Glu Met Ser Gly Pro Val Phe Thr Asp
        140                 145                 150 tcc ggc atc cac atc atc ctc cgc act gag tgagggtggg gagcccaggc        533
Ser Gly Ile His Ile Ile Leu Arg Thr Glu
    155                 160 ctggcctcgg ggcagggcag ggcggctagg ccggccagct cccccttgcc cgccagccag    593
tggccgaacc ccccactccc tgccaccgtc acacagtatt tattgttccc acaatggctg    653 ggaggggggcc cttccagatt gggggccctg ggtccccac tccctgtcca tccccagttg    713
gggctgcgac cgccagattc tcccttaagg aattgacttc agcaggggtg ggaggctccc    773
agacccaggg cagtgtggtg ggagggggtgt tccaaagaga aggcctggtc agcagagccg    833
ccccgtgtcc ccccaggtgc tggaggcaga ctcgagggcc gaattgtttc tagttaggcc    893
acgctcctct gttcagtcgc aaaggtgaac actcatgcgg cagccatggg ccctctgagc    953
aactgtgcag acccttttcac ccccaattaa acccagaacc actaaaaaaa aaaaaaaaa   1013 a                                                                   1014

<210> SEQ ID NO 2
<211> LENGTH: 163
<212> TYPE: PRT
<213> ORGANISM: Homo sapiens

<400> SEQUENCE: 2

Met Ala Asp Glu Glu Lys Leu Pro Pro Gly Trp Glu Lys Arg Met Ser
  1               5                  10                  15
```

-continued

```
Arg Ser Ser Gly Arg Val Tyr Tyr Phe Asn His Ile Thr Asn Ala Ser
            20                  25                  30

Gln Trp Glu Arg Pro Ser Gly Asn Ser Ser Gly Gly Lys Asn Gly
        35                  40                  45

Gln Gly Glu Pro Ala Arg Val Arg Cys Ser His Leu Leu Val Lys His
    50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
                100                 105                 110

Cys Ser Ser Ala Lys Ala Arg Gly Asp Leu Gly Ala Phe Ser Arg Gly
            115                 120                 125

Gln Met Gln Lys Pro Phe Glu Asp Ala Ser Phe Ala Leu Arg Thr Gly
        130                 135                 140

Glu Met Ser Gly Pro Val Phe Thr Asp Ser Gly Ile His Ile Ile Leu
145                 150                 155                 160

Arg Thr Glu
```

```
<210> SEQ ID NO 3
<211> LENGTH: 31
<212> TYPE: DNA
<213> ORGANISM: Homo sapiens

<400> SEQUENCE: 3
gcgcctgcag tatctataya tggaataytg t                              31

<210> SEQ ID NO 4
<211> LENGTH: 31
<212> TYPE: DNA
<213> ORGANISM: Homo sapiens

<400> SEQUENCE: 4
gcgcggatcc rggtttcaga ggktyraasa g                              31

<210> SEQ ID NO 5
<211> LENGTH: 30
<212> TYPE: DNA
<213> ORGANISM: Homo sapiens

<400> SEQUENCE: 5
gcgcgtacca agwccacygt ayattattcc                                30

<210> SEQ ID NO 6
<211> LENGTH: 13
<212> TYPE: PRT
<213> ORGANISM: Artificial Sequence
<220> FEATURE:
<223> OTHER INFORMATION: synthetic peptide

<400> SEQUENCE: 6
```

```
Met Tyr Asp Val Pro Asp Tyr Ala Ser Arg Pro Gln Asn
 1               5                   10
```

```
<210> SEQ ID NO 7
<211> LENGTH: 32
<212> TYPE: PRT
<213> ORGANISM: Artificial Sequence
<220> FEATURE:
<223> OTHER INFORMATION: synthetic peptide
```

```
<400> SEQUENCE: 7

Met Ala Ser Tyr Pro Tyr Asp Val Pro Asp Tyr Ala Ser Pro Glu Phe
1               5                   10                  15

Leu Val Asp Pro Pro Gly Ser Lys Asn Ser Ile Ala Arg Gly Lys Met
            20                  25                  30

<210> SEQ ID NO 8
<211> LENGTH: 39
<212> TYPE: PRT
<213> ORGANISM: Homo sapiens

<400> SEQUENCE: 8

Glu Lys Leu Pro Pro Gly Trp Glu Lys Arg Met Ser Arg Ser Ser Gly
1               5                   10                  15

Arg Val Tyr Tyr Phe Asn His Ile Thr Asn Ala Ser Gln Trp Glu Arg
            20                  25                  30

Pro Ser Gly Asn Ser Ser Ser
            35

<210> SEQ ID NO 9
<211> LENGTH: 39
<212> TYPE: PRT
<213> ORGANISM: Yeast ESS1

<400> SEQUENCE: 9

Thr Gly Leu Pro Thr Pro Trp Thr Val Arg Tyr Ser Lys Ser Lys Lys
1               5                   10                  15

Arg Glu Tyr Phe Phe Asn Pro Glu Thr Lys His Ser Gln Trp Glu Glu
            20                  25                  30

Pro Glu Gly Thr Asn Lys Asp
            35

<210> SEQ ID NO 10
<211> LENGTH: 38
<212> TYPE: PRT
<213> ORGANISM: Homo sapiens

<400> SEQUENCE: 10

Val Pro Leu Pro Ala Gly Trp Glu Met Ala Lys Thr Ser Ser Gly Gln
1               5                   10                  15

Arg Tyr Phe Leu Asn His Ile Asp Gln Thr Thr Thr Trp Gln Asp Pro
            20                  25                  30

Arg Lys Ala Met Leu Ser
            35

<210> SEQ ID NO 11
<211> LENGTH: 38
<212> TYPE: PRT
<213> ORGANISM: Mus musculus

<400> SEQUENCE: 11

Ser Pro Leu Pro Pro Gly Trp Glu Glu Arg Gln Asp Val Leu Gly Arg
1               5                   10                  15

Thr Tyr Tyr Val Asn His Glu Ser Arg Arg Thr Gln Trp Lys Arg Pro
            20                  25                  30

Ser Pro Asp Asp Asp Leu
            35

<210> SEQ ID NO 12
```

```
<211> LENGTH: 38
<212> TYPE: PRT
<213> ORGANISM: Yeast RSPS

<400> SEQUENCE: 12

Gly Arg Leu Pro Pro Gly Trp Glu Arg Thr Asp Asn Phe Gly Arg
1               5                   10                  15

Thr Tyr Tyr Val Asp His Asn Thr Arg Thr Thr Thr Trp Lys Arg Pro
            20                  25                  30

Thr Leu Asp Gln Thr Glu
        35

<210> SEQ ID NO 13
<211> LENGTH: 38
<212> TYPE: PRT
<213> ORGANISM: Homo sapiens

<400> SEQUENCE: 13

Thr Ser Val Gln Gly Pro Trp Glu Arg Ala Ile Ser Pro Asn Lys Val
1               5                   10                  15

Pro Tyr Tyr Ile Asn His Glu Thr Gln Thr Thr Cys Trp Asp His Pro
            20                  25                  30

Lys Met Thr Glu Leu Tyr
        35

<210> SEQ ID NO 14
<211> LENGTH: 37
<212> TYPE: PRT
<213> ORGANISM: Rattus rattus

<400> SEQUENCE: 14

Ser Asp Leu Pro Ala Gly Trp Met Arg Val Gln Asp Thr Ser Gly Thr
1               5                   10                  15

Tyr Tyr Trp His Ile Pro Thr Gly Thr Thr Gln Trp Glu Pro Pro Gly
            20                  25                  30

Arg Ala Ser Pro Ser
        35

<210> SEQ ID NO 15
<211> LENGTH: 14
<212> TYPE: PRT
<213> ORGANISM: Artificial Sequence
<220> FEATURE:
<223> OTHER INFORMATION: consensus sequence

<400> SEQUENCE: 15

Leu Pro Gly Trp Glu Gly Tyr Tyr Asn His Thr Thr Trp Pro
1               5                   10

<210> SEQ ID NO 16
<211> LENGTH: 105
<212> TYPE: PRT
<213> ORGANISM: Homo sapiens

<400> SEQUENCE: 16

His Leu Leu Val Lys His Ser Gln Ser Arg Arg Pro Ser Ser Trp Arg
1               5                   10                  15

Gln Glu Lys Ile Thr Arg Thr Lys Glu Glu Ala Leu Glu Leu Ile Asn
            20                  25                  30

Gly Tyr Ile Gln Lys Ile Lys Ser Gly Glu Glu Asp Phe Glu Ser Leu
        35                  40                  45
```

```
Ala Ser Gln Phe Ser Asp Cys Ser Ala Lys Ala Arg Gly Asp Leu
    50              55                  60

Gly Ala Phe Ser Arg Gly Gln Met Gln Lys Pro Phe Glu Asp Ala Ser
65              70                  75                  80

Phe Ala Leu Arg Thr Gly Glu Met Ser Gly Pro Val Phe Thr Asp Ser
                85                  90                  95

Gly Ile His Ile Ile Leu Arg Thr Glu
            100                 105
```

<210> SEQ ID NO 17
<211> LENGTH: 107
<212> TYPE: PRT
<213> ORGANISM: Yeast ESS1

<400> SEQUENCE: 17

```
His Ile Leu Ile Lys His Lys Asp Ser Arg Arg Pro Ala Ser His Arg
1               5                   10                  15

Ser Glu Asn Ile Thr Ile Ser Lys Gln Asp Ala Thr Asp Glu Leu Lys
                20                  25                  30

Thr Leu Ile Thr Arg Leu Asp Asp Asp Ser Lys Thr Asn Ser Phe Glu
            35                  40                  45

Ala Leu Ala Lys Glu Arg Ser Asp Cys Ser Ser Tyr Lys Arg Gly Gly
    50              55                  60

Asp Leu Gly Trp Phe Gly Arg Gly Glu Met Gln Pro Ser Phe Glu Asp
65              70                  75                  80

Ala Ala Phe Gln Leu Lys Val Gly Glu Val Ser Asp Ile Val Glu Ser
                85                  90                  95

Gly Ser Gly Val His Val Ile Lys Arg Val Gly
            100                 105
```

<210> SEQ ID NO 18
<211> LENGTH: 83
<212> TYPE: PRT
<213> ORGANISM: E. coli

<400> SEQUENCE: 18

```
His Ile Leu Val Lys Glu Glu Lys Leu Ala Leu Asp Leu Leu Glu Gln
1               5                   10                  15

Ile Lys Asn Gly Ala Asp Phe Gly Lys Leu Ala Lys Lys His Ser Ile
                20                  25                  30

Cys Pro Ser Gly Lys Arg Gly Gly Asp Leu Gly Glu Phe Arg Gln Gly
            35                  40                  45

Gln Met Val Pro Ala Phe Asp Lys Val Val Phe Ser Cys Pro Val Leu
    50              55                  60

Glu Pro Thr Gly Pro Leu His Thr Gln Phe Gly Tyr His Ile Ile Lys
65              70                  75                  80

Val Leu Tyr
```

<210> SEQ ID NO 19
<211> LENGTH: 84
<212> TYPE: PRT
<213> ORGANISM: B.subtilis

<400> SEQUENCE: 19

```
His Ile Leu Val Ala Asp Lys Lys Thr Ala Glu Glu Val Glu Lys Lys
1               5                   10                  15

Leu Lys Lys Gly Glu Lys Phe Glu Asp Leu Ala Lys Glu Tyr Ser Thr
                20                  25                  30
```

```
Asp Ser Ser Ala Ser Lys Gly Gly Asp Leu Gly Trp Phe Ala Lys Glu
            35                  40                  45

Gly Gln Met Asp Glu Thr Phe Ser Lys Ala Ala Phe Lys Leu Lys Thr
 50                  55                  60

Gly Glu Val Ser Asp Pro Val Lys Thr Gln Tyr Gly Tyr His Ile Ile
65                  70                  75                  80

Lys Lys Thr Glu

<210> SEQ ID NO 20
<211> LENGTH: 91
<212> TYPE: PRT
<213> ORGANISM: C. jejuni

<400> SEQUENCE: 20

His Ile Leu Val Ala Thr Glu Lys Glu Ala Lys Asp Ile Ile Asn Glu
 1               5                  10                  15

Leu Lys Gly Leu Lys Gly Lys Glu Leu Asp Ala Lys Phe Ser Glu Leu
            20                  25                  30

Ala Lys Glu Lys Ser Ile Asp Pro Gly Ser Lys Asn Gln Gly Gly Glu
        35                  40                  45

Leu Gly Trp Phe Asp Gln Ser Thr Met Val Lys Pro Phe Thr Asp Ala
 50                  55                  60

Ala Phe Ala Leu Lys Asn Gly Thr Ile Thr Thr Thr Pro Val Lys Thr
65                  70                  75                  80

Asn Phe Gly Tyr His Val Ile Leu Lys Glu Asn
                85                  90

<210> SEQ ID NO 21
<211> LENGTH: 67
<212> TYPE: PRT
<213> ORGANISM: A. thaliana

<400> SEQUENCE: 21

Ile Val Ser Lys Ala Asn Phe Glu Glu Val Ala Thr Arg Val Ser Asp
 1               5                  10                  15

Cys Ser Ser Ala Lys Arg Gly Gly Asp Leu Gly Ser Phe Gly Arg Gly
            20                  25                  30

Gln Met Gln Lys Pro Phe Glu Glu Ala Thr Tyr Ala Leu Lys Val Gly
        35                  40                  45

Asp Ile Ser Asp Ile Val Asp Thr Asp Ser Gly Val His Ile Ile Lys
 50                  55                  60

Arg Thr Glu
65

<210> SEQ ID NO 22
<211> LENGTH: 45
<212> TYPE: PRT
<213> ORGANISM: Artificial Sequence
<220> FEATURE:
<223> OTHER INFORMATION: consensus sequence

<400> SEQUENCE: 22

His Ile Leu Val Glu Lys Phe Glu Leu Ala Lys Ser Cys Ser Ser Lys
 1               5                  10                  15

Gly Gly Asp Leu Gly Phe Arg Gly Gln Met Phe Asp Ala Ala Phe Leu
            20                  25                  30
```

-continued

```
Lys Gly Glu Ser Pro Val Thr Gly Tyr His Ile Ile Lys
        35                  40                  45
```

US 7,164,012 B2

NIMA INTERACTING PROTEINS

REFERENCE TO RELATED APPLICATIONS

This application is a continuation of U.S. patent application Ser. No. 09/275,900, filed Mar. 24, 1999, now U.S. Pat. No. 6,596,848. issued Jul. 22, 2003, which is a divisional of U.S. patent application Ser. No. 09/066,074, filed Apr. 24, 1998, now U.S. Pat. No. 5,952,467, issued Sep. 14, 1999, which is a divisional of U.S. patent application Ser. No. 08/555,912, filed Nov. 13, 1995, now U.S. Pat. No. 5,972,697, issued Oct. 26, 1999.

STATEMENT AS TO FEDERALLY SPONSORED RESEARCH

The present invention was made with government support from United States Public Health Services Grant No. CA 37980. The government has certain rights in this invention.

FIELD OF THE INVENTION

The present invention relates generally to the eukaryotic cell cycle and specifically to a novel class of proteins that interact with NIMA protein kinase in the NIMA mitotic pathway.

BACKGROUND OF THE INVENTION

The CDC2 kinase associated with its cyclin partners has been shown to play an important role during G2/M progression in eukaryotic cells. However, recent studies demonstrate that activation of the CDC2 kinase itself is not sufficient to trigger mitosis in some eukaryotic cells such as those in *Saccharomyces cerevisiae* (Amon, et al., *Nature*, 355:368, 1992; Sorger and Murray, *Nature*, 355:365, 1992; Stueland et al., *Mol. Cell. Bio.*, 13:3744, 1993) and *Aspergillus nidulans* (Osmani, et al., *Cell*, 67:283, 1991a). Furthermore, detailed analysis of mouse oocyte maturation reveals that CDC2 histone H1 kinase activity does not increase during the G2/M transition as indicated by germinal vesicle breakdown (GVBD) (Choi, et al., *Development*, 113:789, 1991; Jung, et al., *Int. J. Dev. Biol.*, 37:595, 1993; Gavin, et al., *J. Cell Sci.*, 107:275, 1994). These results suggest that there might be other mitotic activation pathway(s) remaining to be identified.

Recent studies have identified a novel mitotic kinase, NIMA, encoded by the *Aspergillus* nimA gene (Osmani, et al., *Cell*, 53:237, 1988). NIMA kinase activity is tightly regulated during the nuclear division cycle, peaking in late G2 and M. Overexpression of NIMA promotes entry of *Aspergillus* cells into M (Osmani, et al., *Cell*, 53:237, 1988; Lu and Means, *EMBO J.*, 13:2103, 1994). Thus, NIMA is important for progression into mitosis in *Aspergillus*.

NIMA is a protein-Ser/Thr kinase, biochemically distinct from other protein kinases, and its phosphotransferase activity is regulated by Ser/Thr phosphorylation. It has recently been shown that the NIMA mitotic pathway is not restricted to *Aspergillus*, but also exists in vertebrate cells (Lu and Hunter, *Cell*, 8:413, 1995a). In *Xenopus* oocytes, NIMA induces germinal vesicle breakdown without activating Mos, CDC2 or MAP kinase. In HeLa cells, NIMA induces mitotic events without activating CDC2, whereas dominant-negative NIMA mutants cause a specific G2 arrest. In addition, O'Connell, et al (*EMBO J.* 13:4926, 1994) have also demonstrated that NIMA induce premature chromatin condensation in fission yeast and HeLa cells. These results reveal the existence of a NIMA-like mitotic pathway in other eukaryotic cells.

Peptidyl-prolyl cis/trans isomerases (PPIases, proline isomerases) are ubiquitously expressed enzymes catalyzing the cis/trans isomerization of the peptidyl-prolyl peptide bond which can be the rate-limiting step in protein folding or assembly under some circumstances. Cyclophilins and FK506-binding proteins (FKBPs) are two well characterized families of PPIases that share little if any amino acid similarity to each other. However, the members of each family contain a core structure that has been highly conserved from prokaryotes to eukaryotes. The importance of these PPIases is highlighted by the findings that cyclophilin and FK506-binding proteins are the targets of immunosuppressive drugs cyclosporin A and FK506, respectively, and play an important role in cell signaling in T cell activation, although none of these genes have been shown to be essential for life (for review see Schreiber, *Science,* 251:283, 1991; Fruman, et al., *FASEB J.,* 8:391, 1994).

The recent discovery of parvulin has led to the identification of a third family of PPIases, which show little homology with either cyclophilins or FKBPs and is not sensitive to the immunosuppressive drugs (Rahfeld, et al., *FEBS Lett.,* 352:180, 1994a and *FEBS Lett.,* 343:65, 1994b). A sequence homology search identified several other members of this family including those involved in protein maturation and/or transport and the ESS1 gene (Rudd, et al., *TIBS,* 20:12., 1995). ESS1 is an essential gene for the growth in budding yeast and previous results suggested that it may be required at later stages of the cell cycle (Hanes, et al., *Yeast,* 5:55, 1989). ESS1 was recently reisolated as PTF1 in a screen for genes involved in mRNA 3' end maturation. Ptf1 was shown to contain a putative PPIase domain, but PPIase activity could not be demonstrated (Hani, et al., *FEBS Lett.,* 365:198, 1995). So far, none of the PPIases have been shown to be specifically involved in cell cycle control.

There is a need to identify components of the mammalian NIMA mitotic pathway in order to identify genes essential for life. Identification of such genes has several utilities including the identification of appropriate therapeutic targets, candidate genes for gene therapy (e.g., gene replacement), mapping locations of disease-associated genes, and for the identification of diagnostic and prognostic indicator genes, for example.

SUMMARY OF THE INVENTION

The present invention provides a novel class of proteins that associate with NIMA protein kinase. Some of these proteins are characterized by inhibiting the mitosis promoting function of NIMA when overexpressed and inducing mitotic arrest and nuclear fragmentation when depleted.

In a first embodiment, the invention provides an exemplary NIMA associated protein called "protein interacting with NIMA" (Pin1). Pin1 has C-terminal peptidyl-propyl cis/trans isomerase activity and contains a conserved N-terminal tryptophan domain (WW domain) thought to mediate protein-protein interactions. Also included are polynucleotides encoding PIN proteins.

In another embodiment, the invention provides a method for identifying a protein that inhibits the mitosis promoting function of NIMA protein kinase. The method is based on a genetic system designed to detect protein-protein interactions. The method comprises culturing transformed cells containing the following: a nucleic acid construct comprising a DNA binding domain operatively associated with the coding sequence of NIMA, or functional fragments thereof; a nucleic acid library, wherein each member of said library comprises a transactivation domain operatively associated with a protein encoding sequence; and a nucleic acid reporter construct comprising a response element for the DNA binding domain operatively associated with a reporter gene, and monitoring for evidence of expression of reporter gene.

In yet another embodiment, the invention provides a method for controlling the growth of a cell comprising contacting the cell with a composition which modulates Pin1 activity. For examnple, an inhibitor of Pin1 activity such as a PPIase inhibitor or an anti-Pin1 antibody, or an inhibitor of PIN1 expression such as an antisense nucleotide sequence or a ribozyme, can be used to control growth of a cell. Alternatively, Pin1 activity can be increased by an activator or PIN1 expression can be increased by an enhancer, for example.

Finally, the invention provides a method for identifying a protein or other composition (e.g., drug or other small molecule) that associates with and/or modulates Pin1 protein activity or PIN1 gene expression.

BRIEF DESCRIPTION OF THE DRAWINGS

FIG. 1 shows human cDNA clones encoding proteins interacting with NIMA (Pins).

FIG. 2 shows the cDNA and deduced amino acid sequences of human PIN1 and homologies with other WW domain proteins and PPIases. FIG. 2A shows the Pin 1 nucleotide sequence SEQ ID NO: 1) and predicted amino acid sequence SEQ ID NO: 2 (as indicated in one-letter code). The fusion points between GAL4 and Pin 1 in six different isolated clones were: clone H20 at C-9; clone H16.24 and 38 at G+13; clones H6 and H36 at C+15. Underlined residues form a consensus bipartite nuclear localization signal. The N- and C-terminal boxes indicate the WW domain and PPIase domain, respectively. Nucleotide numbers are on the left and amino acid numbers on right. FIG. 2B shows the alignment of the WW domain in selected proteins (from top to bottom SEQ ID NOs: 8–14). FIG. 2C shows the alignment of the PPIase domain in selected proteins (from top to bottom SEQ ID NOs: 15–21). In FIGS. 2B and 2C, Identical residues are shown in the row labeled "Consensus" (SEQ ID NO: 22). Dashes indicate gaps introduced to make the alignment. Cbf2, cell binding factor 2; SC, *S. cerevisiae*; EC, *E. coli*; BS, *B. subtilis*; CJ, *C. jejuni*; AT, *A. thaliana*.

FIG. 5 shows immunoprecipitations to show the interaction between Pin1 and the C-terminal noncatalytic domain of NIMAs in HeLa cells.

DESCRIPTION OF THE PREFERRED EMBODIMENTS

Figures 1A, 1B:
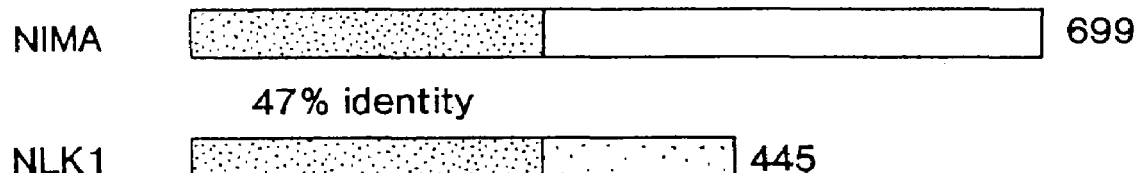
FIG. 1A shows a β-Galactosidase Activity in the two-hybrid system.
FIG. 1B shows a comparison of NIMA and NLK1.

A NIMA-like pathway is required for the $G^2$/M transition in *Aspergillus nidulans* and human cells. The present invention provides the first NIMA-interacting protein, Pin1, of mammalian origin, and methods for identification of other NIMA-interacting proteins. Overexpression of PIN1 and Pin1 activity, induces a specific G2 arrest and delays NIMA-induced mitosis, while depletion of Pin1 triggers mitotic arrest and nuclear fragmentation in budding yeast.

In a first embodiment, the invention provides an isolated mammalian protein characterized as associating with NIMA protein kinase, inhibiting the mitosis promoting function of NIMA when overexpressed, and inducing entry of cells into mitosis when depleted. The C-terminal domain of such a protein catalyzes the cis/trans isomerization of peptidyl-propyl peptide bonds. The N-terminal domain associates with NIMA and contains at least two conserved tryptophan residues (WW domain). While the exemplary polynucleotides and polypeptides of the invention are directed to Pin1, it is understood that any PIN polynucleotide or Pin protein can now be identified and characterized by the methods described herein.

In a preferred embodiment, the present invention provides a substantially pure NIMA-interacting protein (Pin1) characterized by having a molecular weight of about 18 kD as determined by reducing SDS-PAGE, having peptidyl-propyl cis/trans isomerase activity, associating with NIMA protein kinase, and having essentially the amino acid sequence of SEQ ID NO:2. The term "substantially pure" as used herein refers to Pin1 which is substantially free of other proteins, lipids, carbohydrates or other materials with which it is naturally associated. One skilled in the art can purify Pin1 using standard techniques for protein purification. The substantially pure polypeptide will yield a single major band on a non-reducing polyacrylamide gel. The puriry of the Pin1 polypeptide can also be determined by amino-terminal amino acid sequence analysis. Pin1 polypeptide includes functional fragments of the polypeptide, as long as the activity of Pin1 remains. Smaller peptides containing one of the biological activies of Pin1 are therefore included in the invention. Such peptides include immunologically reactive peptides capable of inducing antibody production. The preferred Pin1 of the invention is derived from a human cell.

The invention provides isolated polynucleotides encoding Pin polypeptides. including Pin1. These polynucleotides include DNA, cDNA and RNA sequences which encode Pin1. It is understood that all polynucleotides encoding all or a portion of Pin1 are also included herein, as long as they encode a polypeptide with Pin1 activity. Such polynucleotides include naturally occuring, synthetic, and intentionally manipulated polynucleotides. For example, PIN1 polynucleotide may be subjected to site-directed mutagenesis. The polynucleotide sequence for PIN1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of Pin1 polypeptide encoded by the nucleotide sequence is functionally unchanged. Polynucleotides of the invention include variations thereof which encode the same amino acid sequence, but employ different codons for some of the amino acids, or splice variant nucleotide sequences thereof.

Specifically disclosed herein is a DNA sequence encoding the human PIN1 gene. The sequence contains an open reading frame encoding a polypeptide 163 amino acids in length. The human PIN1 initiator methionine codon shown in FIG. 2A at position 25–27 is the first ATG codon. Preferably, the human PIN1 nucleotide sequence is SEQ ID NO:1 and the deduced amino acid sequence is preferably SEQ ID NO:2 (FIG. 2A).

The polynucleotide encoding Pin1 includes SEQ ID NO:1 as well as nucleic acid sequences complementary to SEQ ID NO:1 (FIG. 2A). A complementary sequence may include an antisense nucleotide. When the sequence is RNA, the deoxynucleotides A, G, C, and T of SEQ ID NO:1 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:2 under physiological conditions. Specifically, the term "selectively hybridize" means that the fragments should hybridize to DNA encoding Pin1 protein under moderate to highly stringent conditions.

Minor modifications of the Pin1 primary amino acid sequence may result in proteins which have substantially equivalent activity as compared to the Pin1 polypeptide described herein. Such proteins include those as defined by the term "having substantially the amino acid sequence of SEQ ID NO:2". Such modifications may be deliberate, as by site-directed mutagenesis, or may be spontaneous. All of the polypeptides produced by these modifications are included herein as long as the biological activity of PIN still exists. Further, deletion of one or more amino acids can also result in a modification of to the structure of the resultant molecule without significantly altering its biological activity. This can lead to the development of a smaller active molecule which would have broader utility. For example, one can remove amino or carboxy terminal amino acids which are not required for Pin1 biological activity.

The Pin1 polypeptide of the invention encoded by the polynucleotide of the invention includes the disclosed sequence (SEQ ID NO:2; FIG. 2A) and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the PIN (e.g., PIN1) polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding PIN can also be obtained by: 1) isolation of double-stranded DNA sequences from the genomic DNA; 2) chemical manufacture of a DNA sequence to provide the necessary codons for the polypeptide of interest; 3) in vitro synthesis of a double-stranded DNA sequence by reverse transcription of mRNA isolated from a eukaryotic donor cell; and PCR of genomic DNA or cDNA using primers capable of annealing to the DNA sequence of interest. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the possible presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for PIN peptides having at least one epitope, using antibodies specific for PIN. Such antibodies can be either polyclonally or monoclonally derived and used to detect expression product indicative of the presence of PIN1 cDNA.

DNA sequences encoding Pin1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the PIN1 polynucleotide sequences may be inserted into a recombinant expression vector. The term "recombinant expression vector" refers to a plasmid, virus or other vehicle known in the art that has been manipulated by insertion or incorporation of the PIN genetic sequences. Such expression vectors contain a promoter sequence which facilitates the efficient transcription of the inserted genetic sequence of the host. The expression vector tpically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, tetracycline responsive promoter or polyhedrin promoters).

Polynucleotide sequences encoding Pin1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the PIN of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies. For example, one of skill in the art could use $(His)_6$ tag affinity purification as described in the EXAMPLES herein.

The Pin polypeptides of the invention can also be used to produce antibodies which are immunoreactive or bind to epitopes of the Pin polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the Pin1 polypeptide of the invention can be prepared using an intact polypeptide or fragments containing small peptides of interest as the immunizing antigen. For example, it may be desirable to produce antibodies that specifically bind to the N- or C-terminal domains of Pin1. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In another embodiment, the invention provides a method for identifying a protein that inhibits the mitosis promoting function of NIMA protein kinase. The method comprises culturing transformed cells containing the following: a nucleic acid construct comprising a DNA binding domain operably associated with the coding sequence of NIMA, or functional fragments thereof; a nucleic acid library, wherein each member of said library comprises a transactivation domain operably associated with a protein encoding sequence; and a nucleic acid reporter construct comprising a response element for the DNA binding domain operably associated with a reporter gene, and monitoring for evidence of expression of reporter gene.

The term "inhibits" refers to a reduction in the mitosis promoting function of NIMA protein kinase. The "mitosis promoting function of NIMA" refers to the ability of NIMA to promote the progression of the G2/M transition in a cell. The term "operably associated" refers to functional linkage between the promoter or regulatory sequence and the controlled nucleic acid sequence; the controlled sequence and regulatory sequence, or promoter are typically covalently joined, preferably by conventional phosphodiester bonds.

The method of the invention comprises culturing cells, under suitable conditions, transformed by standard methods in the art and as described above. The transformed cells contain the followint: a nucleic acid construct comprising a DNA binding domain operably associated with the coding sequence of NIMA, or functional fragments thereof. As used herein, the term "DNA binding domain" refers to a nucleic acid sequence which contains a recognition site for a protein that binds to specific DNA sequences. The coding sequence of NIMA includes nucleic acid sequence that encodes a protein having the biological activity of NIMA as described herein. The method includes "functional fragments" of NIMA that are less than the full length coding sequence but which encode a protein having NIMA biological activity (e.g., Ser/Thr protein kinase).

The transformed cells also contain a nucleic acid library, wherein each member of the library comprises a transactivation domain operably associated with a protein encoding sequence. A "transactivation domain" refers to a nucleic acid sequence which activates transcription, but typically fails to bind to DNA. A nucleic acid library consists of a clone bank of genomic or complementary DNA sequences which are "protein encoding sequences". The term refers to cDNA operably associated with the transactivation domain of a protein as exemplified in the EXAMPLES.

The cells also contain a nucleic acid reporter construct comprising a response element for the DNA binding domain operably associated with a reporter gene. As used herein, the term "reporter" refers to a gene encoding a trait or a phenotype which permits the monitoring and selection of, or the screening for, a cell containing the marker, and thus a NIMA interacting protein. The nucleic acid reporter is a selectable marker such as a color indicator (e.g., lacZ). Other suitable reporter genes will be known to those of skill in the art.

The protein-protein interaction system exemplified in the EXAMPLES herein preferably utilize the GAL4 protein to provide the DNA binding and transactivation domains (Fields and Song, *Nature*, 340:245, 1989). Other nucleic acid constructs comprising the coding sequences of proteins that have a DNA binding and transactivation domain will be known to those of skill in the art and can be utilized in the method of the invention for providing the hybrid constructs.

The method of the invention relies on interaction between the library encoded protein and the NIMA protein, or functional fragment thereof, in order to activate transcription of the reporter gene. Once the library encoded protein and the NIMA protein associate, they bring the DNA binding domain and the transactivation domain in close proximity, resulting in transcriptional activity. Thus, the method provides a means for identifying a protein that interacts or associates with NIMA protein kinase.

While the method of the invention as described above is preferred, it is understood that the transformed cell may contain the reverse constructs, e.g., a nucleic acid construct comprising a transactivation domain operably associated with the coding sequence of NIMA, or fragments thereof, and a nucleic acid library, wherein each member of said library comprises a DNA binding domain operably associated with a protein encoding sequence.

Also included in the present invention are NIMA interacting proteins identified by the above method.

The invention also provides a method for controlling the growth of a cell comprising contracting the cell with a composition which modulates Pin1 activity. The term "modulate" envisions the suppression of expression of PIN1 or suppression of Pin1 activity, when it is over-expressed, or augmentation of PIN1 expression or Pin1 activity when it is under-expressed. Growth of a cell is "controlled", for example, by inhibiting mitosis promoting function of NIMA or inducing entry of cells into mitosis. An inhibitor of Pin1 activity or protein level, for example, would result in arrest in mitosis. Therefore, Pin1 activity or protein level can be decreased, leading the cell to mitotic arrest, or alternatively, Pin1 activity or protein level can be increased, arresting the cells in G2.

Where controlling the growth of a cell is associated with the expression of PIN1 polynucleotide, nucleic acid sequences that interfere with PIN1 expression at the translational level can be used. This approach utilizes, for example, antisense nucleic acid, ribozymes, or triplex agents to block transcription or translation of a specific PIN mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids primarily work via RNaseH-mediated degradation of the target mRNA. Antisense may also interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target PIN-producing cell. The use of antisense methods is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991: Helene. C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

Other Pin inhibitors include PPIase inhibitors. For example, immunosuppressive drugs such as cyclosporin A and FK506, are PPIase inhibitors useful in the method of the invention for inhibiting some Pin proteins. The Pin1 or other Pin protein of the invention is useful for screening for other inhibitors as well. For example, a suspected PPIase inhibitor is incubated with Pin1 protein under suitable conditions to allow Pin1 enzymatic activity to be expressed and measured, and the level of activity in the presence and absence of the inhibitor is assayed to determine the effect on Pin1 activity.

Pin1 activity may also be increased in the presence of an activator. PIN1 expression may be increased in the presence of an enhancer for example. Stimulation of Pin1 activity or overexpression of PIN1 arrests the cells in G2 and inhibits the mitosis promoting function of NIMA. The cis-acting elements which control genes are called promoters, enhancers or silencers. Promoters are positioned next to the start site of transcription and function in an orientation-dependent manner, while enhancer and silencer elements, which modulate the activity of promoters, are flexible with respect to their orientation and distance to the start site of transcription. One of skill in the art will know methods for stimulating expression of PIN1 by including an enhancer, for example, to stimulate PIN1 expression. The effect of an enhancer or other regulatory element can be determined by standard methods in the art (e.g., Northern blot analysis, nuclear runoff assay).

Pin1 activity can be affected by an activator. An "activator" as used herein includes a protein or a small molecule, such as an organic compound, for example, which increases Pin1 activity or protein level, such that a cell arrests in G2. An activator can be identified by incubating Pin1 and a putative activator under conditions that allow interaction between the components, and measuring of the effect of the activator on Pin1. For example, one could determine whether cells were arrested in G2 (e.g., increased Pin1 activity), or whether cells continued to cycle through G2 to M (e.g., by FACS analysis or labeled nuclei analysis).

The Pin1 protein of the invention is useful in a screening method to identify compounds or compositions which affect the activity of the protein or expression of the gene. Thus, in another embodiment, the invention provides a method for identifying a composition which affects Pin1 comprising incubating the components, which include the composition to be tested (e.g., a drug or a protein) and Pin1, under conditions sufficient to allow the components to interact, then subsequently measuring the effect the composition has on Pin1 activity or expression. The observed effect on Pin1 may be either inhibitory or stimulatory. For example, the entry of cells into mitosis or G2 arrest can be determined by nuclear content (e.g., immunofluorescence or FACS analysis based on DNA content) or other methods known to those of skill in the art.

The increase or decrease of PIN1 transcription/translation can be measured by adding a radioactive compound to the mixture of components, such as $^{32}$P-ATP (for nuclei) or $^{3}$H-Uridine, or $^{35}$S-Met, and observing radioactive incorporation into PIN1 transcripts or protein, respectively. Alternatively, other labels may be used to determine the effect of a composition on PIN1 transcription/translation. For example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation. Analysis of the effect of a compound on PIN1 is performed by standard methods in the art, such as Northern blot analysis (to measure gene expression) or SDS-PAGE (to measure protein product), for example. Further, Pin1 biological activity can also be determined, for example, by incorporation label into nuclei.

The method of the invention described above also includes identifying a protein that associates with Pin1 protein. The method comprises incubating the protein with Pin1 protein, or with a recombinant cell expressing Pin1, under conditions sufficient to allow the components to interact and determnining the effect of the protein on Pin1 activity or expression. Alternatively, one of skill in the art could use the two-hybrid system described above to identify a protein that interacts or associates with Pin1 protein. Once identified, such Pin/PIN-associated proteins may now be used as targets for drug development.

In another embodiment, the invention provides a method for treating a cell proliferative disorder. The method comprises administering a subject in need of such treatment, an amount of Pin1 inhibitor effective to induce entry of cells into mitosis or apoptosis. The "amount of Pin1 inhibitor effective to induce entry of cells into mitosis" means that the amount of polypeptide, peptide, polynucleotide, or monoclonal antibody for example, which when used, is of sufficient quantity to ameliorate the disorder. The term "cell-proliferative disorder" denotes malignant as well as non-malignant cell populations which morphologically often appear to differ from the surrounding tissue both morphologically and genotypically. Malignant cells (i.e. cancer) develop as a result of a multistep process. The PIN1 polynucleotide that is an antisense molecule is useful in treating malignancies of the various organ systems. For example, the method may be useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, leukemia, breast cancer, non-small cell carcinoma of the lung, cancer of the small intestine, and cancer of the esophagus. Essentially, any disorder which is etiologically linked to altered expression of PIN1 could also be considered susceptible to treatment with a PIN1 suppressing/inhibiting reagent.

The method is also useful in treating non-malignant or immunologically-related cell-proliferative diseases such as psoriasis, *pemphigus vulgaris,* Bechet's syndrome, acute respiratory distress syndrome (ARDS), ischemic heart disease, post-dialysis syndrome, rheumatoid arthritis, acquired immune deficiency syndrome, vasculitis, lipid histiocytosis, septic shock and inflammation in general. Essentially, any disorder which is etiologically linked to PIN1 would also be considered susceptible to treatment.

For purposes of the invention, an antibody or nucleic acid probe specific for Pin1 may be used to detect Pin1 polypeptide (using antibody) or polynucleotide (using nucleic acid probe) in biological fluids or tissues. The invention provides a method for detecting a cell proliferative disorder which comprises contacting an anti-Pin1 antibody or nucleic acid probe with a cell suspected of having a Pin1 associated disorder and detecting binding to the antibody or nucleic acid probe. The antibody reactive with Pin1 or the nucleic acid probe is preferably labeled with a compound which allows detection of binding to Pin1. Any specimen containing a detectable amount of antigen or polynucleotide can be used. The level of Pin1 in the suspect cell can be compared with the level in a normal cell to determine whether the subject has a Pin1-associated cell proliferative disorder. Preferably the subject is human.

When the cell component is nucleic acid, it may be necessary to amplify the nucleic acid prior to binding with an PIN1 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Various viral vectors which can be utilized for gene therapy as taught herein include adenovirus, herpes viris, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. Other viral vectors include DNA vectors such as adenovirus and adeno-associated virus (AAV). All of these vectors can transfer or incorporate a gene for a selectable marker so that transduced cells can be identified and generated. By inserting a PIN1 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by usin an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the PIN1 antisense polynucleotide. In addition, the viral vector may contain a regulatory element such as a tetracycline responsive promoter (inducible or repressible) operably linked to a polynucleotide sequence).

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\Psi 2$, PA317 and PA12, for example. These cell lines produce empty virions, since no genome is packaged. If a retroviral vector is introduced into such cells in which the packazing signal is intact, but the structural genes are replaced by other genes of interest, the vector can be packaged and vector virion produced.

Another targeted delivery system for PIN1 polynucleotides (e.g., antisense) is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivers vehicles in vitro and in vivo. It has been shown that larvae uni-lamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficienct while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The following examples are intended to illustrate but not limit the invention. While they are typical of those that might be used, other procedures known to those skilled in the art may alternatively be used.

EXAMPLE 1

Materials and Methods

1. Yeast Two-Hybrid Screen and cDNA Isolation

For the yeast two-hybrid screen, the *Aspergillits nidulans* nimA cDNA was inserted into the pAS2 vector (from S. Elledge; HHMI, Baylor University) (Durfee et al., 1993; Harper, et al., 1993) as fusion to GAL4 DNA-binding domain, resulting in NIMA/PAS2. A HeLa cell two-hybrid cDNA library that contained inserts fused to the transactivation domain of GAL4 (residue 768–881) (obtained from D. Beach; HHMI, Cold Spring Harbor Laboratory, New York Nov. 12, 1995) (Hannon et al., 1993) was contransformed with NIMA/PAS2 into the yeast reporter strain Y190, which was then plated on yeast drop-out media lacking Leu. Trp and His containing 35 mM 3-amino-1,2,4 triazole and about $10^5$ transformants were analyzed as described previously (Harper et al., 1993). To determine the interaction properties of isolated clones, K40M NIMA, NIMA280–699$_{fs}$ NLK1 and a frame-shift mutant NIMA280–699$^{fs}$ (a base pair deletion at the litigation point) were also subcloned into the pAS2 vector, followed by cotransformation into Y190 cells with the isolated cDNA clones. To obtain additional PIN1 5' untranslated sequence, a HeLa cell cDNA library constructed by R. Fukunaga; Salk Institute, La Jolla, Calif.) was screened with the H20 cDNA fragment. DNA sequence was determined by the dideoxynucleotide chain termination method.

2. Isolation of Human NIMA-Like Kinase 1 (NLK1)

For polymerase chain reaction (PCR), three degenerate oligonucleotides GCGCCTGCAGTATCTATAC/TATG-GAATAT/CTGT/(SEQ ID NO: 3) GCGCGGATCCG/AG-GTTTCAGAGGT/GTC/TG/AAAG/CAG (SEQ ID NO: 4) and GCGCGTACCAAGT/ACCACT/CGTAC/TATTAT-TCC (SEQ ID NO: 5) were designed specifically to the catalytic domain V, VII and VIII, respectively, which are conserved among NIMA (Osmani et al., *Cell*. 53:237, 1988), NPK, a budding yeast NIMA-related kinase (Schweitzer and Philippsen, *Mol. Gen. Geneti.*, 34:164, 1992) and human HsPK21 (Schultz and Nigg, *J. Cell. Growth Differ.*, 4:821, 1993). Human placenta cDNA library (from R. Evans, Salk Institute, La Jolla, Calif.) was used as a template. The PCR cycle was 1 min at 95° C., 2 min at 42° C. and 3 min at 63° C. PCR products with the expected size were subcloned and sequenced. Three potential clones (Ping-1, -44 and -77) were consistently obtained and showed a high sequence identity to NIMA at the deduced amino acids. To obtain the full length cDNA sequence, the Ping-1 PCR product was used as a probe to screen HeLa cell cDNA library filters provided by X. D. Fu (Gui et al., *Nature*, 369:678, 1994); over thirty positive clones were obtained and encode the same protein, referred to as NLK1 (NIMA-like kinase 1). NLK1 cDNA is 2152 bp and encodes 445 amino acids with an apparent molecular weight of 45 kDa on a SDS-polyacrylamide gel. NLK1 was found to be same as NEK2 reported later by Schultz et al. (*Cell. Growth Differ.*, 5:625, 1994)

3. DNA Transfection and Indirect Immunofluorescence Microscopy

NIMA and its derivative mutant expression constructs were the same as described previously (Lu and Hunter, *Cell.* 81:413, 1995a). For expression of Pin1, an HA tag (MYD-VPDYASRPQN) (SEQ ID NO:6) was added to the N-terminus of PIN1 clones H20 and H6, followed by insertion into pUHD 10-3 vector as described previously (Lu and Means, *EMBO J.*, 13:2103, 1994). Transfection of the tTA-1 cell line (Gossen and Bujard, *Proc. Natl. Acad. Sci. USA,* 89:5547, 1992) was described previously (Elredge et al., *Meth. Enzymol.*, 254:481, 1995) with the exception that cells were plated at lower density (30%), which seemed to increase the transfection efficiency and the percentage of cycling cells. Indirect immunofluorescence microscopy was performed as described (Lu and Hunter, *Cell,* 81:413, 1995a). The dilution of primary antibodies was: mouse M2 mAb (Kodak/IBI.IgaG1 isotype), 1:600; 12CA5 mAb (IgG2b isotype, 1:1500: SC35 mAb (from X. Fu, IgG1 isbtype) (Fu and Maniatis, *Nature,* 343:437, 1990); straight supernatant; and rabbit anti-PML antibodies (from R. Evans) (Dyck et al., *Cell.* 76:333, 1994), 1:100. The FITC-conjugated goat anti-mouse IgG1 and Texas Red-conjugated goat anti-mouse IgG2b secondary antibodies (Southern Biotechnology) were used at 1:50, with no significant cross-reactivity. Cells were observed and photographed with a Zeiss microscope, or an MRC-1000 laser-scanning confocal assembly (BioRad).

4. Flow Cytometry Analysis

Cells were harvested 48 hr after transfection and stained with the 12CA5 MAb, followed by flow cytometry analysis on a Becton-Dickinson FACScan machine (Lu and Hunter, *Cell,* 81:413, 1995a). 12CA5-negative or -positive cells ($10^4$) were collected to determine the DNA content, and cell cycle profiles were determined using the M Cycle analysis software (Phoenix Flow Systems, San Diego, Calif.).

5. Metabolic Labeling, Immunoprecipitation and Immunoblot Analysis

Metabolic labeling of tTA-1 cells was as described previously (Lu and Hunter, *Cell.* 81:413, 1995a). Cells were lysed in a NP40 lysis buffer (50 mM Tris-HCl, pH 8.0, 0.1% NP40, 200 mM NaCl, 20 mM β-glycerophosphate, 20 mM NaF, 0.1 mM sodium orthovanadate, 50 μg/ml phenylmethylsufonyl fluoride, 10 μg/ml leupeptin, 10 μg/ml aprotinin, and 1 mM DTT or 10 mM β-mercaptoethanol (in the case of $Ni^{2-}$-NTA agarose precipitation) and preclarified with boiled *S. aureis* or $Ni^{2-}$-NTA agarose (Qiagen). The lysates were then incubated with M2or 12CA5 or $His-Pin1-Ni^{2})^-$-NTA agarose. After washing 6 times with lysis buffer, the precipitates were subjected to SDS-polyacrylamide, gel electrophoresis and immunoblotting.

6. Expression and Purification of Pin1 and Kinase Assays

To express the $(His)_6$ tag-containing Pin1 protein, the cDNA insert from H20 clone was subcloned into SpeI/HindIII sites of pProEx1 and the recombinant protein was expressed in and purified from BL21 bacterial strain using $Ni^{2-}$-NTA agarose column (Qiagen) as described by the manufacturer. To examine whether Pin1 could be phosphorylated, recombinant Pin1 protein was added to NIMA kinase reaction mixtures at concentrations up to 0.5 mg/ml, with β-casein and PL1 pepcide as positive controls, as described previously (Lu et al., *J. Biol. Chem.*, 269:6603, 1994). The effect of Pin1 on NIMA was assayed using PL1 as a substrate with increasing concentrations of recombinant Pin1 (Lu et al., *J. Biol. Chem.*, 269:6603, 1994). Cyclin B/CDC2 (obtained from N. Watanabe; Salk Institute) ERK1 MAPK (obtained from R. Fukunaga) and PKA (Promega) were assayed using histone H1, myelin basic protein and H1 as substrates respectively.

7. PPIase Assay

PPIase activity of the purified recombinant proteins was assayed using the procedure of Heitman et al. (*Methods,* 5:176, 1993) with the following exceptions. The reaction was carried out 5° C. and chymotrypsin was added just betore the peptide substrate (N-Succ-Ala-Pro-Phe-p-nitroanilide, Sigma). The cis to trans isomerization was monitored every 6 seconds by a change in the absorbance at 395 nm using DMS 2000 UV and Visible Spectrophotometer (Varian). FKBP, cyclosporin A and FK520, a FK506 derivative, were gifts of D. Schultz and C. Zuker, University of California, San Diego.

8. Yeast Complementation Assays

PIN1 expression was driven from the strong constitutive yeast triose phosphate isomerase promoter (TPI) (Smith et al., 1985). Plasmid pTPI-PIN1 was made by insertion of an ~850 bp BamHI-XhoI fragment of PIN1 cDNA (from H20/GADGH) into pJK305-TPI (J. Kamens, Ph.D. Thesis, Harvard University, 1991). PTPI-PIN1 directs the synthesis of the native full length Pin1 protein and carries the yeast 2μ replicator and LEU2 selectable marker. Plasmid YepHESS carries the yeast ESS1 gene, a 2μ replicator and HIS3 selectable marker (Hanes et al., *Yeast,* 5:55, 1989).

For tetrad analysis, a heterozygous ESS1 disruption strain MGG3/pSH-U (MATα/MATα ura3/ura3 leu2/leu2 his3/his3 ess1::URA3/ESS1) (Hanes et al., *Yeast,* 5:55, 1989), was transformed with control vector pJK305-TPI, YepHESS, or pTPI-PIN1. Cells were induced to undergo sporulation on 1% potassium acetate plates, tetrads were dissected and haploid segregants grown for 3–4 days at 30° C. on rich medium (YEPD) plates. Only tetrads that showed proper segregation of the URA3, and MATa and MATα alleles were included in the viable spore counts. For the curing experiment, a homozygous disruption derivative of MGG3/pSH-U (relevant genotype ess1::URA3/ess1::URA3) carrying ESS1 on episomal plasmid (YepHESS) was transformed with either pJK305-TPI or pTP1-PIN1. Cells were serially passaged once per day (1/50 Dilutions) for 6 days in liquid completer synthetic medium lacking leucine; thus maintaining selection for the PIN1-expressing plasmid or control vector (2μ, LEU2), but not for the ESS1-bearing plasmid (2 μM, HIS3). Cells were plated and phenotypes of individual colonies scored by replica plating to appropriate selective media.

9. PIN1-Decendent Yeast and Determination of Terminal Phenotype

For Pin1 depletions experiments in yeast, we used the GAL1 promoter (Yocum et al., *Mol. Cell. Bio.*, 4:1985, 1984). Plasmid pGAL-PIN1, was made by insertion of a SpeIXohI fragment of the PIN1 cDNA from pN2P1/GADGH into AvrII and XhoI cut pBC103. PGAL-PIN1 directs the synthesis of an HA1 hemagglutinin epitope-tagged version of Pin1 that contains a 31 amino-terminal extension (MASYP YDVPDYASPEFLVDPPGSKNSIARGKM) (SEQ ID NO:7) where underlined residues are the HA1 epitope and the normal PIN1 initiator, respectively. Other residues derive from polylinker sequences. An integrating version, I-GAL-PIN1, was made by removal of the GAL-PIN1 cassette from pGAL-PIN1 with Xba1 and SacI and reinsertion into the same sites in pRS305 (Sikorski and Hieter, *Genetics.* 122:19, 1989). I-GAL-PIN1 carries a LEU2 selectable marker.

The original ess1 knockout strain (MGG3/pSH-U) does not grow in galactose, probably due to a gal2 mutation. Therefore, to make a strain (YSH12) that lacks ESS1 function and whose growth depends on a galactose-inducible version of PIN1, the following scheme was used. A gal strain, FY86 (MATa his3Δ200 ura3–52 leu2Δ1) was transformed with integrating vector GAL-PIN1 (LEU2). Leu transformants were mated with a haploid MGG3/pSH-U segregant (MATa ura3 his3 leu2 ess1::URA3) carrying YEpHESS. Diploids were sporulated and tetrads dissected on rich medium containin 2% galactose/1% raffinose. Haploid segregants that contained the ess1::URA3 disruption (ura) and GAL-PIN1 (leu), but lacked YEpHESS (his) were identified. Isolates that showed growth on galactose (YEPG) but not on glucose (YEPD) medium ere further characterized. Cells that did not contain the ess1 knockout (ura) but did contain GAL-PIN1 (leu) were used as controls. Inducible expression of PIN1 in several isolates of YSH12 was confirmed by immunoblot analysis.

To shut off expression of PIN1 in ess1-0 cells, strain YSH12 was grown overnight in galactose or galactose/glucose-containing medium and inoculated (~1/50 dilution) into glucose containing-medium. Cells were grown for approximately 12 hours and then reinoculated into fresh glucose-containing medium for an additional 18 hours. Aliquots of cells were harvested by centrifugation, fixed by the addition of 70% ethanol and stored at 4° C. Bud size distribution was scored under DIC (Normarski) illumination after cells were resuspended in water and sonicated extensively to disperse clumped cells. For DAPI staining, the fixed cells were stained with 1 µg/ml DAPI and mounted in 75% glycerol and photographed under fluorescent illumination. FACS analysis of yeast cells was described previously (Sazer and Sherwood, *J. Cell Sci.,* 509, 1990).

EXAMPLE 2

Identification of Clones Encoding Proteins Interacting With NIMA (PINS)

To search for human cDNAs encoding proteins able to interact with NIMA, a yeast two-hybrid system that uses GAL4 recognition sites to regulate expression of both HIS3 and LacZ (Durfee et al., *Genes Dev.,* 7:555, 1993) was used. As bait, the full length coding sequence of the *Aspergillus nidulans nimA* was fused to the C-terminus of the GAL4 DNA-binding domain in pAS2 driven by a partially ADH promoter (Harper, et al., *Cell,* 75:805, 1993). As prey, we used the GAL4 transactivation domain and a human HeLa cell cDNA fusion library driven by the highly active entire ADH promoter, resulting in high level expression (Hannon, et al., *Genes Dev.,* 2378, 1993). Initially, Y190 cells were transformed with the NIMA/pAS2 expression vector in an attempt to establish stable strains constitutively expressing NIMA, but the transformant colonies were very small and could not be propagated. The failure of the transformants to grow is probably due to the fact that NIMA induces mitotic arrest in budding yeast, as it does in the other different eukaryotic cells so far examined (Osami, et al., *Cell,* 53:237, 1988; Lu and Means, *EMBO J.,* 13:2103, 1994; O'Connell et al., *EMBO J.,* 13:4926, 1994: Lu and Hunter, *Cell,* 81:413, 1995a). To circumvent this problem, Y190 yeast cells were cotransformed with NIMA/pAS2 and the two-hybrid screen cDNA library in the hope that expression of one or more of the cDNA library products might rescue the lethal phenotype of NIMA.

Out of $10^6$ colonies screened, 13 were consistently positive upon repeat transformations. The specificity of the interaction was tested using full length NIMA, a C-terminal noncatalytic fragment of NIMA, NIMA280–699, and a human NIMA-like kinase 1 (NLK1) (FIG. 1A). FIG. 1A shows a β-Galactosidase activity in the two-hybrid system. Yeast strain Y190 was cotransformed with vectors expressing the three different types of cDNA and different domains of NIMA or NLK1 as indicated, and grown in SC media lacking Trp and Leu, followed by β-galactosidase activity filter assay as described previously (Durfee, et al., *Genes Dev.,* 7:55, 1993). NLK1, which was isolated from a human placenta cDNA library and proved to be the same as Nek2 (Schultz et al., *Cell Growth Differ.,* 5:625, 1994), is 47% identical to NIMA in its catalytic domain, but NIMA and NLK1 has very little similarity in their C-terminal noncatalytic domains (FIG. 1B). Based on the sequences of their inserts and the specificities of their interaction with NIMA and NLK1, these clones fell into three different cene classes, referred to as PIN1, PIN2 and PIN3 (PIN=protein interacting with NIMA). There were six PIN1, three PIN2 and four PIN3 clones. The analysis of the two-hybrid interactions indicate Pin3 interacts with the catalytic domains in both NIMA and NLK1s, whereas Pin1 and Pin2 interact with the C-terminal domain of NIMA. The followings examples focus on Pin1 as an exemplary Pin protein.

EXAMPLE 3

Analysis of the PIN1 CDNA

Figure 3:
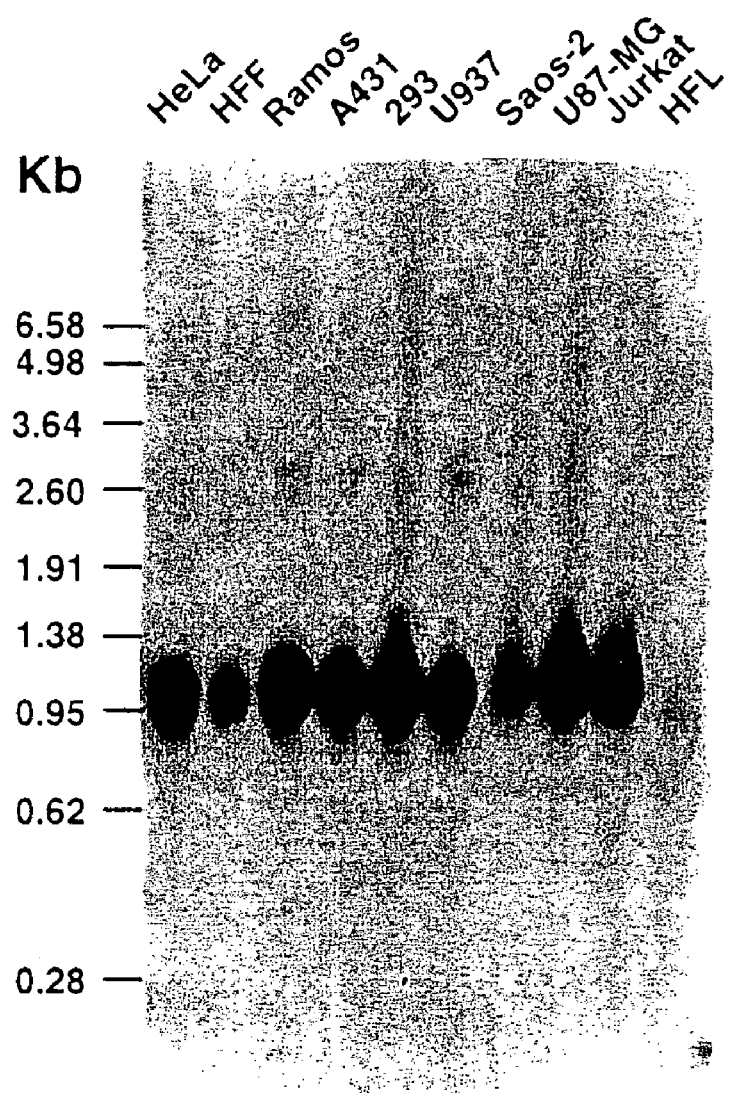
FIG. 3 shows an analysis of PIN1 mRNA expression in human cell lines and human fetal liver. HeLa, epitheloid carcinoma cells; HFF, human foreskin fibroblasts; Ramos, Burkitt lymphoma cells; A431, epitheloid carcinoma cells; 293; adenovirus E1A transformed human embryonic kidney cells; U937, histiocytic lymphoma cells; Saos-2, osteosarcoma cells; U87-MG, glioblastoma cells; Jurkat, T leukemia cell line and HFL, human fetal liver. Position of the RNA molecular weight standards (Promega) are on the left.

The DNA and deduced amino acid sequence of the protein encoded by the longest PIN1 cDNA (1.0kb) is shown in FIG. 2A. It encodes a protein of 163 amino acids with the predicted molecular weight of 18,245. When expressed in HeLa cells, Pin1 migrated with an apparent size of ~18 kDa in an SDS-polyacrylamide gel. Pin1 shows a high similarity to the budding yeast Ess1 protein (Hanes et al., *Yeast,* 5:55, 1989). Based on recent RNA primer-extension studies and reexamination of the nucleotide sequence of ESS1 (Hani et al., *FEBS Lett.,* 365:198, 1995), it is likely that the second ATG is used as the initiation codon, rather than the first ATG as originally proposed (Hanes et al., *Yeast,* 5:55, 1989); in addition, a G should be inserted at position 919, which results in a C-terminal frame shift. The corrected ESS1 sequence encodes a 169 amino acid protein with 45% identity to Pin1. Northern blot analysis of human cell line and human fetal liver RNAs showed that there is a single PIN1 mRNA of ~1.0 kb present in all cell lines and tissue tested (FIG. 3). Fifteen µg of the indicated total RNAs wsere run on each lane, HeLa, epitheloid carcinoma cells: HFF, human foreskin fibroblasts: Ramos, Burkitt lymphoma cells; A431, epitheloid carcinoma cells; 293; adenovirus E1A transformed human embryonic kidney cells; U937, histiocytic lymphoma cells; Saos-2, osteosarcoma cells; U87-MG, glioblastoma cells; Jurkat, T leukemia cell line and HFL, human fetal liver. Position of the RNA molecular weight standards (Promega) are on the left.

These results, together with the sequence comparison between Pin1 and Ess1, confirm the authenticity of the PIN1 open reading frame, although there is no inframe termination condon preceding the putative initiation site. Sequence analysis of six different PIN1 cDNA clones identified the points of fusion with the GAL4 activation domain at Arg–

(−3), Glu+(+5) and Lys−(+6), indicating that the N-terminal 5 amino acids of Pin1 are not necessary for the interaction with NIMA. Immunoblot analysis using anti-Pin1 antibodies confirmed that Pin1 is an 18 kD protein in the cell.

The deduced Pin1 sequence contains two identifiable domains, an N-terminal WW domain and C-terminal putative PPIase domain. The WW domain contains two invariant Trp residues and other residues highly conserved in the WW domains of other proteins including mammalian dystrophins and Yap, and the yeast Rsp1 and Ess1 (Sudol et al., 1995). However, the Cys or His-rich domain flanking the WW domain found in WW domain-containing proteins including Ess1 (Sudol et al., 1995) is not conserved in the human Pin1. The C-terminal two-thirds of Pin1 contains motifs that are characteristic of the recently identified third family of PPIases (Rudd et al., TIBS, 20:11, 1995). The PPIase domain of Pin1 contains three highly observed subdomains, with 45% identity to parvulin and 62% identity to a partial PPIase from A. thaliana. A putative nuclear localization signal is located in the beinning of the PPIase domain, which is also conserved in Ess1.

FIG. 2A shows the predicted Pin1 amino acid sequence is indicated in one-letter code. The fusion points between GAL4 and Pin1 in six different isolated clones were: clone H20 at C−9; clone H16, 24 and 38 at G+13; clones H6 and H36 at C+15. Underlined residues form a consensus bipartite nuclear localization signal. The N- and C-terminal boxes indicate the WW domain and PPIase domain. Nucleotide numbers are on the left and amino acid numbers on right. FIGS. 2B and 2C show alignments of the WW domain (B) and PPIase Domain (C) in selected proteins. Identical residues are shown in the bottom row. Dashes indicate gaps introduced to make the alignment. Cbf2, cell bindinrg factor 2; SC, S. cerevisiae; EC, E. coli; BS, B. subtilis; CJ, C. jejuni; AT, A. thaliana.

EXAMPLE 4

Pin1 Has PPIase Activity

Figure 4A:
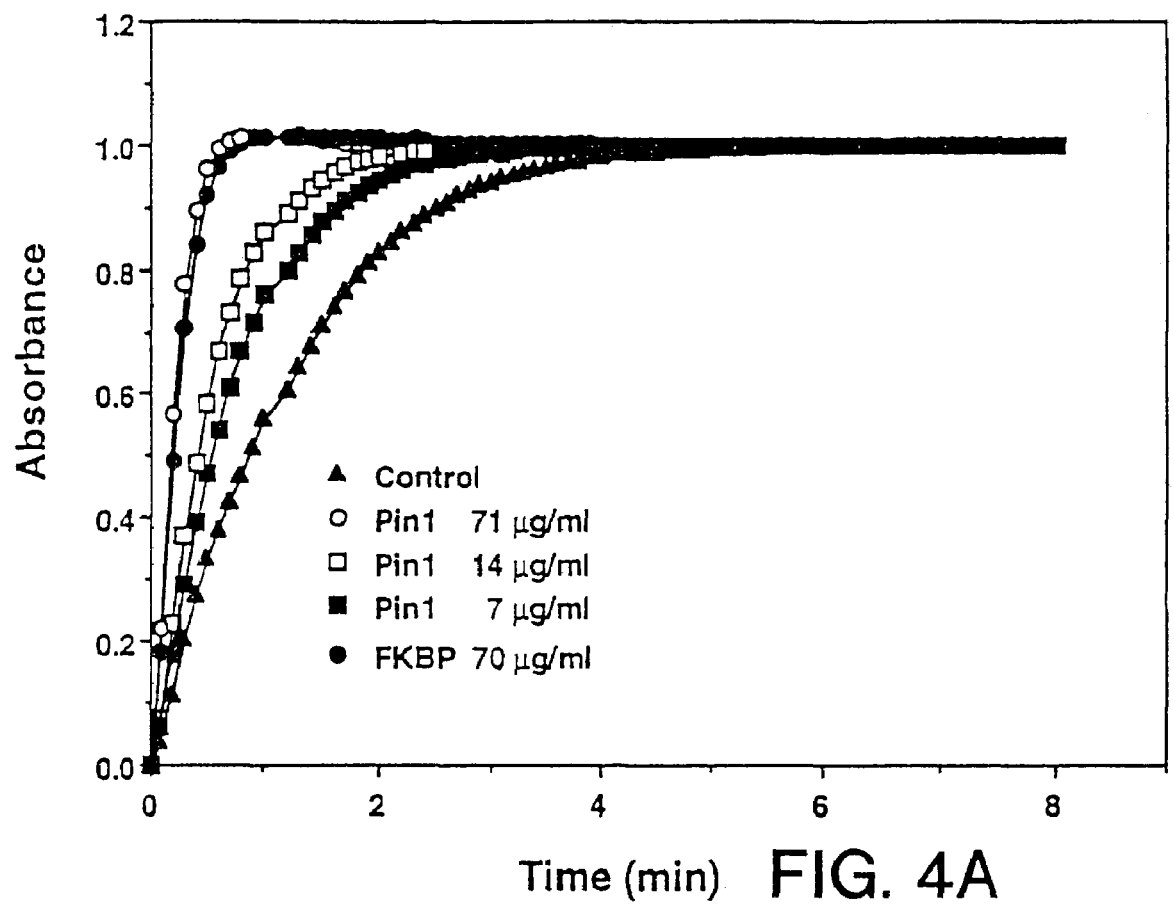
FIG. 4 shows the PPIase activity of Pin1. Different concentrations of Pin1 were used as indicated, with the recombinant FK506-binding protein (FKBP) PPIase being used as a positive control. The control sample contained all the ingredients except the PPIase. The insert shows PPIase activity during the first min of assay.
Figure 4B:
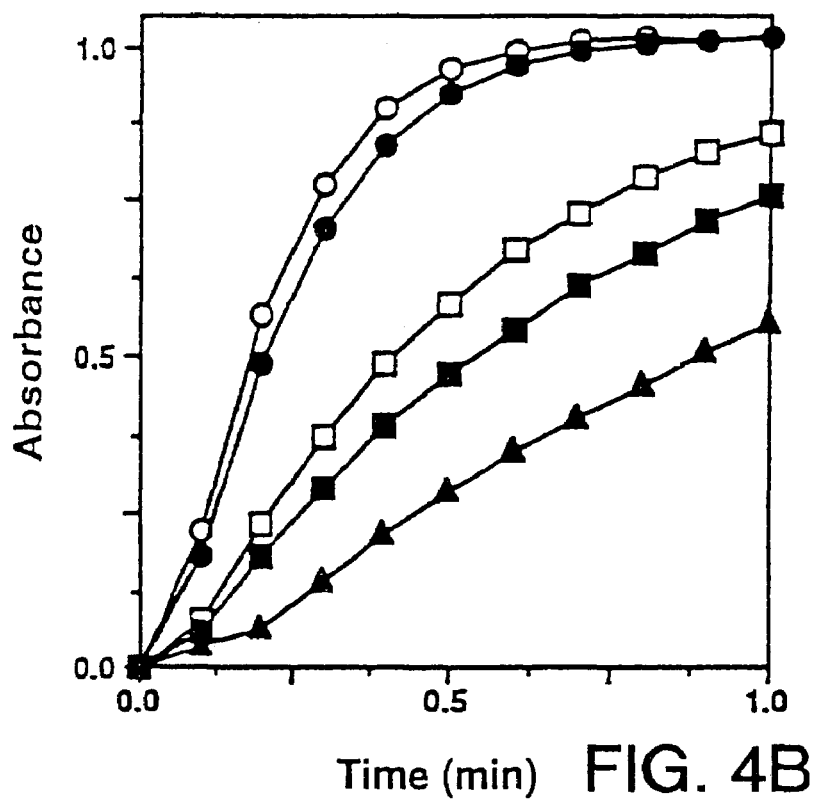

Because of the strong sequence similarity between Pin1 and the third PPIase family, Pin was tested to determine if Pin could catalyze the cis/trans isomerization of peptidylprolyl peptide bonds in vitro, a characteristic of PPIase. Pin1 was expressed in bacteria with an N-terminal (His)$_6$ tag and was purified from bacteria using, a Ni$^{2-}$-NTA agarose column. When purified recombinant Pin1 was tested for PPIase activity using a standard chymotrypsin-coupled spectrophotometric assay (Heitman et al., Methods, 5:176, 1993), PPIase activity was readily detected which was highly concentration-dependent, with a specific activity similar to that of recombinant FKBP (FIG. 4). The isomerase activity was measured as described in Example 1. The cis to trans isomerization was monitored every 6 seconds by a change in the absorbance at 395 nm, with the finally stable absorbance of each sample being set at 1.0. Different concentrations of Pin1 were used as indicated, with the recombinant FK506-binding protein (FKBP) PPIase being used as a positive control. The control sample contained all the ingredients except the PPIase. The insert shows PPIase activity during the first minute of the assay (▲control; ○Pin1, 71 µg/ml; □Pin1, 14 µg/ml; ■Pin1, 7 µg/ml; ●FKBP 70 µg/ml).

Like parvulin, the PPIase activity of Pin1 was not inhibited by either cyclosporin A or FK520, a derivative of FK506, even at 25 µM. These results contirm that Pin1 is a to member of the third family of PPIase.

EXAMPLE 5

Pin1 Interacts With the C-Terminal Domain of NIMA

In the two-hybrid system, Pin1 interacted with NIMA, kinase-negative K40M NIMA and C-terrminal NIMA280–699, but not with NLK1 (Table 1), indicating that NIMA interacts specifically with the C-termnal non-catalytic domain of NIMA in yeast. To determine if there was a stable interaction between Pin1 and NIMA in HeLa cell extracts, recombinant Pin1 was coupled to beads to determine whether NIMA could be recovered from lysates of cells transiently expressing different NIMA mutants. Since NIMA induces mitotic arrest (Lu and Hunter, Cell, 81:413, 1995a), it is difficult to express sufficient wild type NIMA to detect complex formation, but since Pin1 interacted with the kinase-negative K40M NIMA as efficiently as wild type NIMA in the yeast two-hybrid system, we used K40N NIMA and truncated derivative mutant constructs were used.

Figures 5A, 5B, 5C, 5D, 5E:
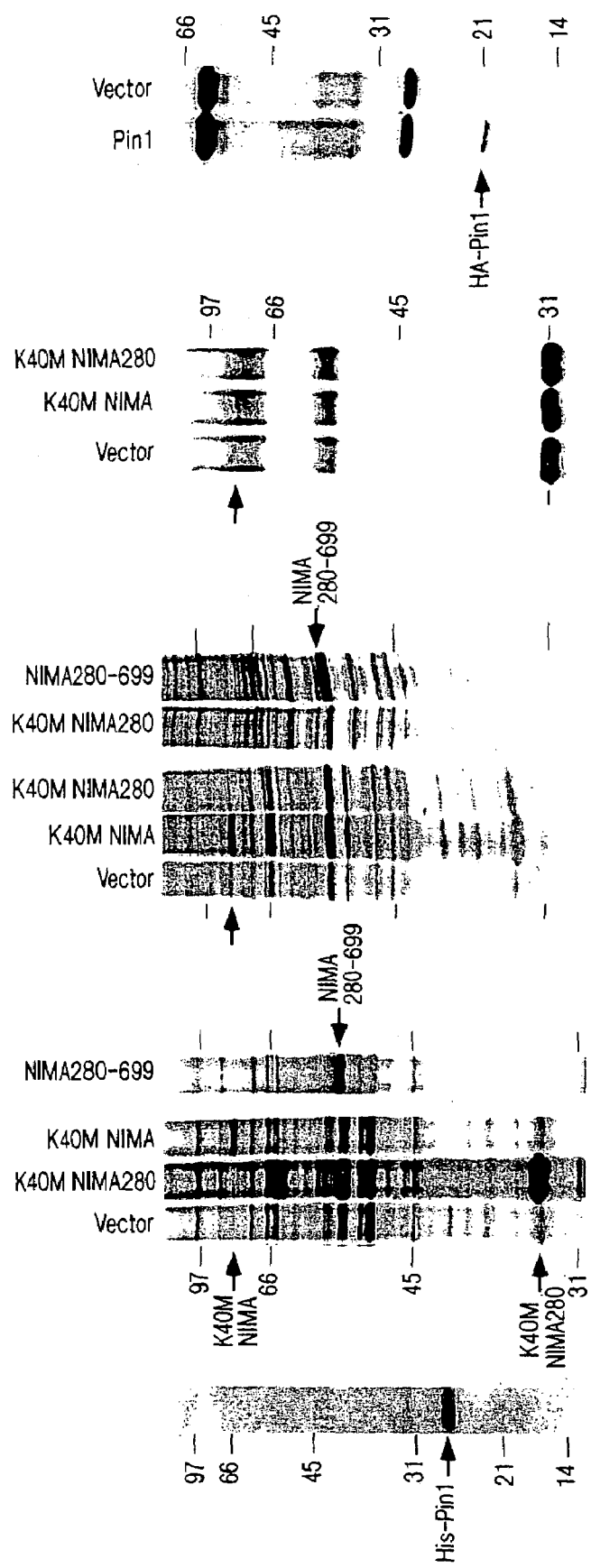
FIG. 5A shows the expression and purification of His-Pin1. The PIN1 cDNA was subcloned into pProEx1 and the recombinant protein was purified from bacteria using $NI^{2-}$-NTA agarose column, followed by analyzing the protein on a 15% SDS-containing gel, and Coomassie staining. The positions of His-Pin1 and standard size markers are indicated.
FIG. 5B shows the expression of NIMAs in HeLa cells. tTA-1 cells were transfected with different FLAG-tagged NIMA constructs and labeled with $^{35}S$ Express Label for 24 hr, followed by immunoprecipitation using the M2 mAb. The precipitated proteins were analyzed on a 10% SDS-containing gel followed by autoradiography. The positions of K40M, NIMA, K40M NIMA280, NIMA280–699 and standard size mrarkers are indicated.
FIG. 5C shows a stable complex between recombinant Pin1 and NIMAs. Cell lysates similar to those in panel B were incubated with His-Pin1-$Ni^{2-}$-NTA bead, as indicated in panel A and washed, followed by electrophoresis on an SDS-containing gel and autoradiography.
FIGS. 5D and 5E show coimmunoprecipitation of K40M NIMA with Pin1. tTA-1 cells were cotransfected with FLAG-tagged NIMA and HA-PIN1 constructs for 24 hr. Cell lysates were immunoprecipitated with the HA-specific 12CA5 mAb, followed by immunoblotting using the M2 mAB specific for the FLAG tag (D) and vice versa (E).

FIG. 5 shows immunoprecipitations to show the interaction between Pin1 and the C-terminal noncatalytic domain of NIMAs in HeLa cells. FIG. 5A shows the expression and purification of His-Pin1. The PIN1 cDNA was subcloned into pProEx1 and the recombinant protein was purified from bacteria using Ni$^{2-}$-NTA agarose column, followed by analyzing the protein on a 15% SDS-containing gel, and Coomassie staining. The positions of His-Pin1 and standard size markers are indicated. FIG. 5B shows the expression of NIMAs in HeLa cells. tTA-1 cells were transfected with different FLAG-tagged NIMA constructs and labeled with $^{35}$S Express Label for 24 hr, followed by immunoprecipitation using the M2 mAb. The precipitated proteins were analyzed on a 10% SDS-containing gel followed by autoradiography. The positions of K40M, NIMA, K40M NIMA280, NIMA280–and standard size markers are indicated. FIG. 5C shows a stable complex between recombinant Pin1 and NIMAs. Cell lysates similar to those in panel B were incubated with His-Pin1-Ni$^{2-}$-NTA bead, as indicated in panel A and washed, followed by electrophoresis on an SDS-containing gel and autoradiography. FIGS. 5D and 5E show coimmunoprecipitation of K40M NIMA with Pin1. tTA-1 cells were cotransfected with FLAG-tagged NIMA and HA-PIN1 constructs for 24 hr. Cell lysates were immunoprecipitated with the HA-specific 12CA5 mAb, followed by immunoblotting using the M2 mAB specific for the FLAG tag (D) and vice versa (E).

Out of several different fusion proteins tested, His-Pin1 was found to be most stable and easiest to purify in large quantities when expressed in bacteria (FIG. 5A). When incubated with 35S-labeled extracts from cells transiently expressing the full length K40M NIMA, an N-terminal fragment K40M NIMA280, or a C-terminal fragment NIMA280–699 (FIG. 5B), the recombinant His-Pin1 beads specifically bound K40M NIMA and NIMA280–699, but not K40M NIMA280 (FIG. 5C). Results also showed that purified GST-NIMA 280–699 directly interacts with purified Pin1 in vitro. These results indicate that the recombinant Pin1 interacts with C-terminal domain of NIMA in the HeLa cell extracts.

To examine whether a Pin1 and NIMA complex is formed in the cell, an HA epitope tag was inserted at the N-terminus of Pin1 and coexpressed it with FLAG-tagged NIMA constructs in HeLa cells using a tetracycline-responsive expression system, as described previously (Lu and Hunter, Cell, 81:413, 1995a). When cell lysates were immunoprecipitated with the HA tag-specific mAb (12CA5), followed by immunoblot analysis using the M2mAb specific for the FLAG tag and vice versa, K40M NIMA but not K40M NIMA280 was detected in Pin1 immunoprecipitates (FIG. 5D). Conversely, Pin1 was detected only in K40M NIMA immunoprecipitates (FIG. 5E). When the isolated catalytic domain of NIMA was expressed in HeLa cells, it was located in the cytosol (Lu and Hunter, *Cell,* 81:413, 1995a), whereas Pin1 is a nuclear protein (see below); therefore it is unlikely that Pin1 interacts with the NIMA catalytic domain. These results, together with the in vitro binding assay and the two-hybrid analysis, suggest that the C-terminal noncatalytic domain of NIMA is involved in the interaction with Pin1.

To examine whether Pin1 affected NIMA kinase activity, purified recombinant Pin1 protein was added to a NIMA kinase reaction mixture in the presence of absence of the PL1 peptide substrate. Under these conditions tested, Pin1 was neither phosphorylated by nor inhibited NIMA kinase. Similar results were obtained with several other protein kinases including cyclin B/CDC2, ERK1 and PKA. These results indicated that Pin1 is unlikely to act as a substrate or an inhibitor of the NIMA, CDC2, EPK1 and PKA protein kinases.

EXAMPLE 6

Pin1 Colocalizes With NIMA in a Defined Nuclear Substructure

To examine whether Pin1 is colocalized with Nima in human cells, the subcellular localization of Pin1 was determined using indirect immunofluorescence staining as described previously (Lu and Hunter, *Cell,* 81:413, 1995a). When Ha-tagged Pin1 was expressed in HeLa cells and stained with the 12A5 mAB, Pin1 was observed almost exclusively in the nucleus. This result indicates that Pin1 is a nuclear protein, consistent with the presence of a nuclear localization signal in Pin1 (FIG. 2A). Confocal microscopy further revealed that although Pin1 was distributed throughout the nucleus, it was highly concentrated in certain areas with a speckled appearance (FIG. 6, right panel).

Figure 6:
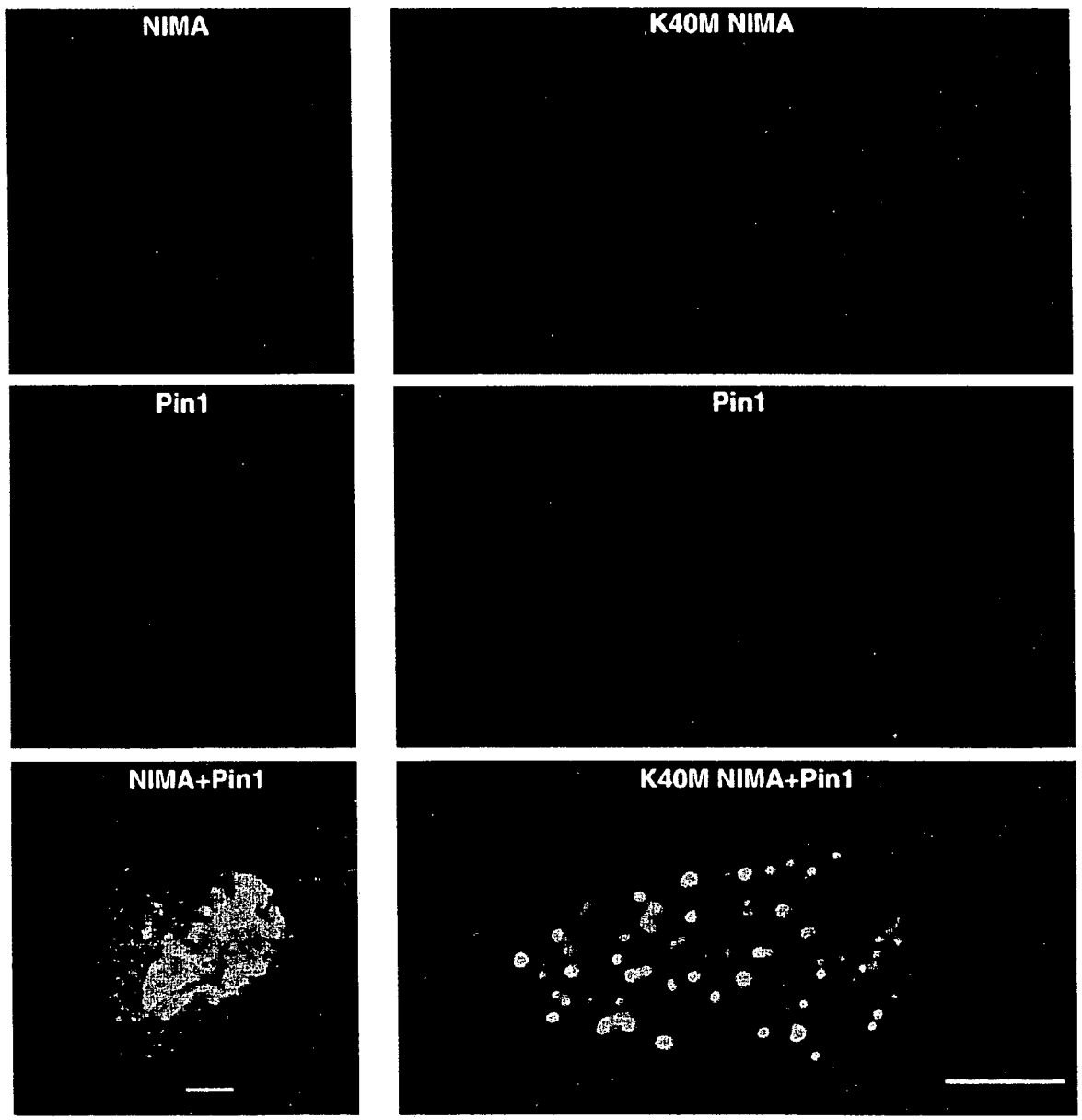
FIG. 6 shows the colocalization of Pin1 and NIMA and its kinase-negative mutant in HeLa Cells. Twenty four hr after transfection with the vectors expressing HA-tagged Pin1 only (right panels) or HA-tagged Pin1 and FLAG-tagggged NIMA (left panels) or its kinase-negative mutant (K40M NIMA, middle panels), the transfected tTA-1 cells were processed for indirect immunofluorescence staining and examined by confocal microscopy. Top panels: staining pattern for NIMA or K40M NIMA obtained with FLAG tag-specific M2 mAb or SC-35 obtaining with anti-SC-35 mAb, and then FITC-conjugated IgG1-specific secondary antibodies; middle panels: staining pattern for Pin1 obtaining with HA tag-specific 12CA5 mAb and Texas-Red-conjugated IgG2b-specific secondary antibodies; bottom panels: double-staining for Pin1 and NIMA, Pin1 and K40M NIMA, or Pin1 and SC-35 displayed by superimposing the respective top and middle images, with yellow color indicating colocalization. Arrows point to an untransfected cell, indicating very little cross reactivity among the antibodies. Bar, 1 µm.

FIG. 6 shows the colocalization of Pin1 and NIMA and its kinase-negative mutant in HeLa Cells. Twenty four hr after transfection with the vectors expressing HA-tagged Pin1 only (right panels) or HA-tagged Pin1 and FLAG-tagged NIMA (left panels) or its kinase-negative mutant (K40M NIMA, middle panels), the transfeected tTA-1 cells were processed for indirect immunofluorescence staining and examined by confocal microscopy. Top panels: staining pattern for NIMA or K40M NIMA obtained with FLAG tag-specific M2 mAb or SC-35 obtaining with anti-SC-35 mAb, and then FITC-conjugated IgG1-specific secondary antibodies; middle panels: staining pattern for Pin1 obtaining with HA tag-specific 12CA5 mAb and Texas-Red-conjugated IgG2b-specific secondary antibodies; bottom panels: double-staining for Pin1 and NIMA. Pin1 and K40M NIMA, or Pin1 and SC-35 displayed by superimposing the respective top and middle images, with yellow color indicating colocalization. Arrows point to an untransfected cell, indicating very little cross reactivity among the antibodies, Bar. 1 µm.

To examine whether Pin1 and NIMA were colocalized in HeLa cells, HA-tagged PIN1 and Flag-tagged nimA or its kinase-negative mutant (K40M nimA) cotransfected into tTA-1 cells and then examined the localization of expressed proteins using tag-specific 12CA5 and M2 mAbs and isotope-specific secondary antibodies. In cells with the NIMA-induced mitotic phenotype (FIG. 6, left panels), Pin1 was associated with the condensed chromatin, but was also distributed throughout the cell, as was NIMA (Lu and Hunter, 1995a). In K40M NIMA-expressing cells, Pin1 was concentrated in nuclear substructures, where the mutant NIMA was also concentrated (FIG. 6, middle panels). The colocalization was extensive, but not complete (FIG. 6, middle lower panel). Pin1 was also colocalized with the C-terminal NIMA280–699 in the nuclear substructures. Since similar nuclear substructures have been observed by immunostaining with anti-SC35 splicing factor (Fu and Maniatis, *Nature,* 343:437, 1990) and anti-PML antibodies (Dyck et al., *Cell,* 76:333, 1994), Pin1 nuclear substructures were examined to determine whether they were the same as those localized by SC35 or PML. When cells expressing Pin1 were doubly stained with 12CA5 and anti-splicing factor SC35 or anti-PML antibodies, the speckles displayed by Pin1 were found to be the same as those detected using anti-SC35 (FIG. 6, right panels), but not anti-PML antibodies. These results indicate that Pin1 and K40M NIMA are colocalized in the spliceosome nuclear substructure. Since using identical protocols, completely different localization patterns were observed for several other proteins, including the human NLK1 which was colocalized with Pin3 in the nucleolus, the localization pattern of Pin1 and NIMA is unlikely to be due to a nonspecific accumulation in certain areas of the nuclease resulting from over expression. Therefore, these results demonstrate that Pin1 is colocalized with NIMA in the nucleus in a defined nuclear substructure.

EXAMPLE 7

Pin1 Overexpression Inhibits NIMA-Induced Mitotic Arrest and Induces G2 Arrest in HeLa Cells In the yeast two-hybrid system, expression of Pin1 rescued the lethal phenotype of NIMA, indicating that Pin1 might inhibit the mitotic function of NIMA. To examine whether over expression of Pin1 in HeLa cells blocked NIMA-induced mitotic arrest, cells were contransfected with expression vectors for nimA and either PIN1 or an expression vector control and their phenotypes examined, as described previously (Lu and Hunter, *Cell,* 81:413, 1995a).

FIG. 7 shows overexpression of PIN1 delays NIMA-induced mitotic arrest and induces a specific G2 arrest in HeLa cells. FIG. 7A shows the results og tTA-1 cells cotransfected with nimA and PIN1 or control vector. At the times indicated, cells were fixed and doubly labeled with M2 mAb and Hoechst dye, followed by scoring for the percentage of cells with rounding and chromatin condensation in a sample of at least 250, NIMA-expressing cells. The data are the average from two independent experiments. FIGS. 7B, C, and D show after transfection with PIN1 expression vector or the control vector for 48 hr, tTA-1 cells were stained with the 12CA5 mAb and then with FITC-conjugated secondary antibodies and propidium iodide, followed by FACS analysis. Based on the FITC intensity of the PIN1-transfected cells, cells were divided into two populations with 12CA5-negative (B) or -positive cells (C), and cell cycle profiles were determined to compare with those in total vector-transfected cells (A).

Figure 7A:
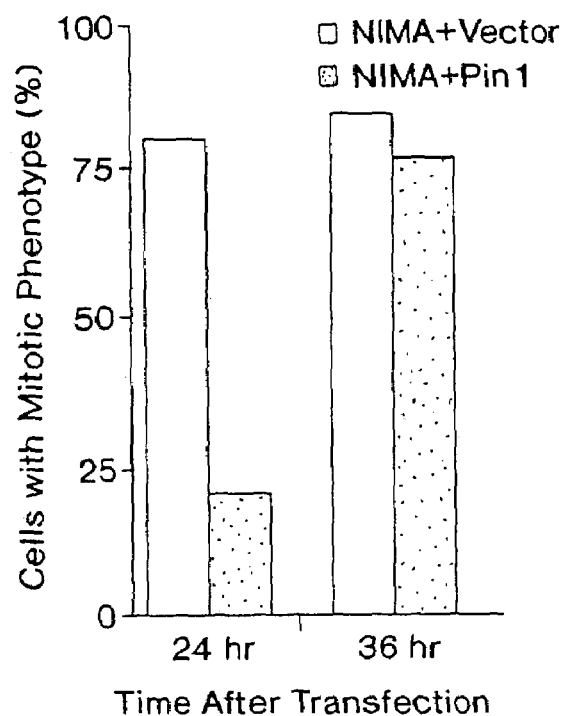
FIG. 7A shows the results of tTA-1 cells cotransfected with nimA and PIN1 or control vector. At the times indicated, cells were fixed and doubly labeled with M2 mAb and Hoechst dye, followed by scoring for the percentage of cells with rounding and chromatin condensation in a sample of at least 250 NIMA-expressing cells. The data are the average from two independent experiments.

At 24hr after transfection, ~80% of NIMA-expressing cells were rounded up and contained highly condensed chromatin (FIG. 7A). When cells were contransfected with nimA and PIN1, NIMA was expressed at much higher levels than in cells contransfected with nimA and control vector, as detected by immunofluorescence microscopy. However, at 24 hr only ~21% of NIMA-expressing cells showed the complete mitotic phenotype. The other NIMA-expressing cells were not completely rounded up and their chromatin was not as condensed as those in cells expressing only NIMA (FIG. 5 left panels and 7A), although by 36 hr all the NIMA-expressing cells displayed the mitotic phenotype (FIG. 7A). These results indicated that Pin1 can partially inhibit the mitosis-promoting function of NIMA.

Figure 7B:
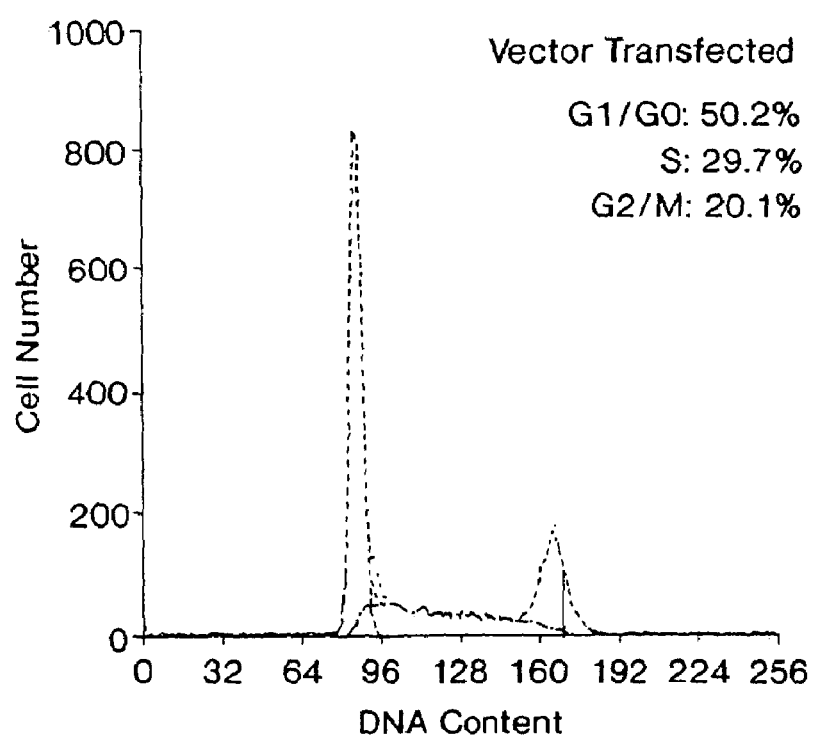
FIGS. 7B, C, and D show after transfection with PIN1 expression vector or the control vector for 48 hr, tTA-1 cells were stained with the 12CA5 mAb and then with FITC-conjugated secondary antibodies and propidium iodide, followed by FACS analysis. Based on the FITC intensity of the PIN1-transfected cells, cells were divided into two populations with 12CA5-negative (B) or -positive cells (C), and cell cycle profiles were determined to compare with those in total vector-transfected cells (A).
Figure 7C:
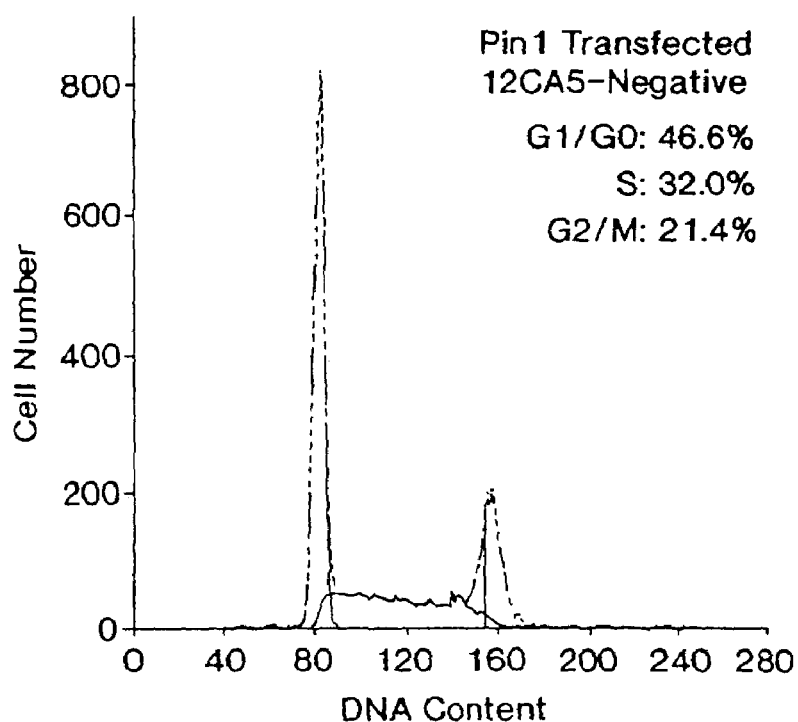
FIG. 7 shows overexpression of PIN1 delays NIMA-induced mitotic arrest and induces a specific G2 arrest in HeLa cells.
Figure 7D:
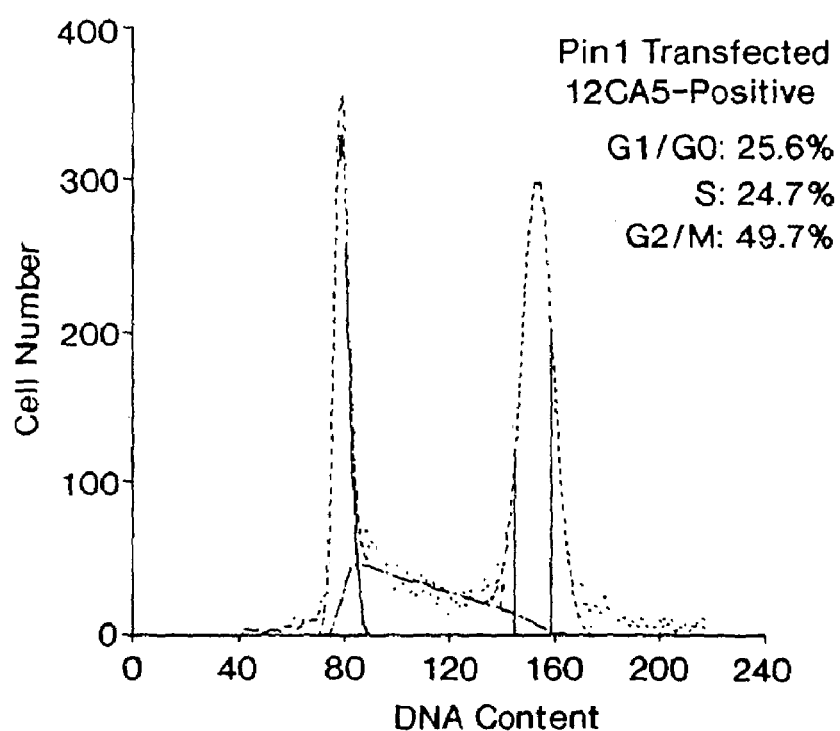

To examine whether overexpression of Pin1 blocked the G2/M transition. HeLa cells were transfected with either PIN1 or the control vector and cycle progression was examined by immunofluorescence microscopy and FACS analysis. Cells expressing Pin1 contained a large interphase nucleus, and it was very difficult to find mitotic cells expressing Pin1, suggesting that Pin1 might induce a G2 arrest. FACS analysis indicated that the percentage of cells with 4 n DNA content was significantly increased in cells expressing Pin1 (12CA5-positive) (FIG. 7D). About 50% of cells were in G2, with commensurately fewer cells in G1 and S. Similar results were also obtained with over expression of another independent PIN1 clone (H6) encoding a 5 amino acid N-terminal deletion mutant. In contrast, the vector-transtected cells showed very little 12CA5 staining and displayed a similar cell cycle profile to that of cells not expressing Pin1 (12CA5-negative) in the Pin1-transfected cell population (FIGS. 7B and C). These results, together with the delaying effect of Pin1 on NIMA-induced mitotic arrest, suggest that Pin1 can inhibit the NIMA pathway which is required for the G2/M transition.

EXAMPLE 8

PIN1 is a Functional Homologue of the Essential ESS1 Gene of S. Cerevisiae

Overexpression of Pin1 inhibits the G2/M transition in HeLa cells as shown above. If this inhibitory effect is due to the fact that high levels of Pin1 affect a cell cycle checkpoint control, depletion of Pin1 should promote the G2/M transition, resulting in a mitotic arrest. To examine this possibility, budding yeast were used where endogenous protein expression can be readily manipulated. Since Pin1 shows striking similarity to the yeast Ess1, the human PIN1 was tested to determine whether it might functionally substitute for the yeast gene. Since ESS1 knockout mutations are lethal in yeast (Hanes et al., Yeast, 5:55, 1989), the ability of PIN1 to restore viability to ess1-mutants was asigned. First, plasmids that express PIN1 under the control of a constitutive yeast promoter were introduced into diploid cells in which one copy of ESS1 is disrupted (ess1::URA3/ESS1). Cells were induced to undergo sporulation, tetrads were dissected, and viability of the resulting haploid spores was scored (Table 1A). As expected, tetrads derived from cells transforned with vector alone showed a 2:2 segregation for spore viability (viable:inviable). In contrast, ~25% of the tetrads from cells transformed with a PIN1-expressing plasmid showed 4:0 seregation for spore viability, indicating that PIN1 complements the ess1– mutant to allow spore outgrowth and haploid cell viability. PIN1 did not complement ess1– mutant to allow spore outgrowth and haploid cell viability. PIN1 did not complement ess1– mutants quite as efficiently as ESS1 itself, where more than half the tetrads from cells bearing an ESS1 plasmid showed a 4:0 segregation from spore viability. Growth curves revealed that PIN1-expressing ess1– cells had doubling times only slightly longer than control cells. Thus, human PIN1 can functionally substitute for ESS1 in haploid yeast cells.

Second, the PIN1 expression plasmid was introduced into diploid cells in which both chromosomal copies of ESS1 are disrupted (ess1::URA3/ess1::URA3) but that remain viable by maintaining a plasmid-borne copy of ESS1. If PIN1 functionally substitute for ESS1, then it should be possible to cure cells of the ESS1 plasmid. Table 1B shows that cells serially passaged in media selecting only for the PIN1 plasmid (LEU2) lost the ESS1 plasmid (HIS3) about 12% of the time, whereas cells containing a control vector did not lose the ESS1 plasmid. Thus, human PIN1 can functionally substitute for ESS1 in diploid yeast cells.

TABLE 1

PIN1 Complements the ESS1 Knockout Mutation in Budding Yeast

A. Tetrad Analysis

| Plasmid | Total Tetrads | Number of Viable Spores per Tetrad | | | | |
|---|---|---|---|---|---|---|
| | | 0 | 1 | 2 | 3 | 4 |
| Vector | 21 | 0 | 3 | 17 | 1 | 0 |
| PIN1 | 83 | 5 | 6 | 46 | 6 | 20 |
| ESS1 | 29 | 0 | 0 | 6 | 6 | 17 |

B. Curing Experiment

| Plasmid | His$^+$/Leu$^+$ | Ura$^+$ | Loss of PIN1 plasmid (%) |
|---|---|---|---|
| Vector | 216/216 | 216 | 0 |
| PIN1 | 380/431 | 431 | 12 |

A. PIN1 rescues ess1– lethality in haploids. The heterozygous disruption strain MGGS3/pSH-U was transformed with an ESS1- or PIN1-expression vector plasmid or control vector. Cells were induced to undergo sporulation and tetrads were dissected. The number of viable spores included only those that showed proper segregation of independent markers. As expected, almost all segregants that were ura$^-$ (i.e. carried the ess1::URA3 knockout allele) were also his$^-$ or leu$^+$ indicating the presence of the ESS or PIN1 containing plasmid, respectively.

B. PIN1 permits loss of ESS1-containing plasmids in a ess1 diploid knockout strain. A diploid disruption strain (ess1::URA3/ess1::URA3) carrying the ESS1 -plasmid (HIS3) was transformed with the vector alone (LEU2) or a PIN1-expression vector plasmid (LEU2). Cells were serially passaged in leucine-deficient media that maintains selection for control or the PIN1 plasmid but not for the ESS1 plasmid. Cells were plated and phenotypes of individual colonies scored by replica plating to appropriate selective media. Loss of the ESS1 plasmid is detected by loss of the his$^+$ phenotype, while the presence of PIN1 is detected by a leu$^-$ phenotype. A ura$^+$ phenotype confirms the presence of the knockout allele (ess1::URA3).

EXAMPLE 9

Depletion of PIN1/ESS1 Results in Mitotic Areest and Nuclear Fragmentation in S. Cerevisiae To examine the effect of depleting Pin1/Ess1 on the cell cycle, PIN1 driven by the regulated GAL promoter was introduced into an ess1 yeast strain. As expected, Pin1-expressing strains grew normally in inducing media (galactose) or noninducing media (galactose/glucose, with a basal level of PIN1 expression), but did not grow in repressing media (glucose).

Figure 8:
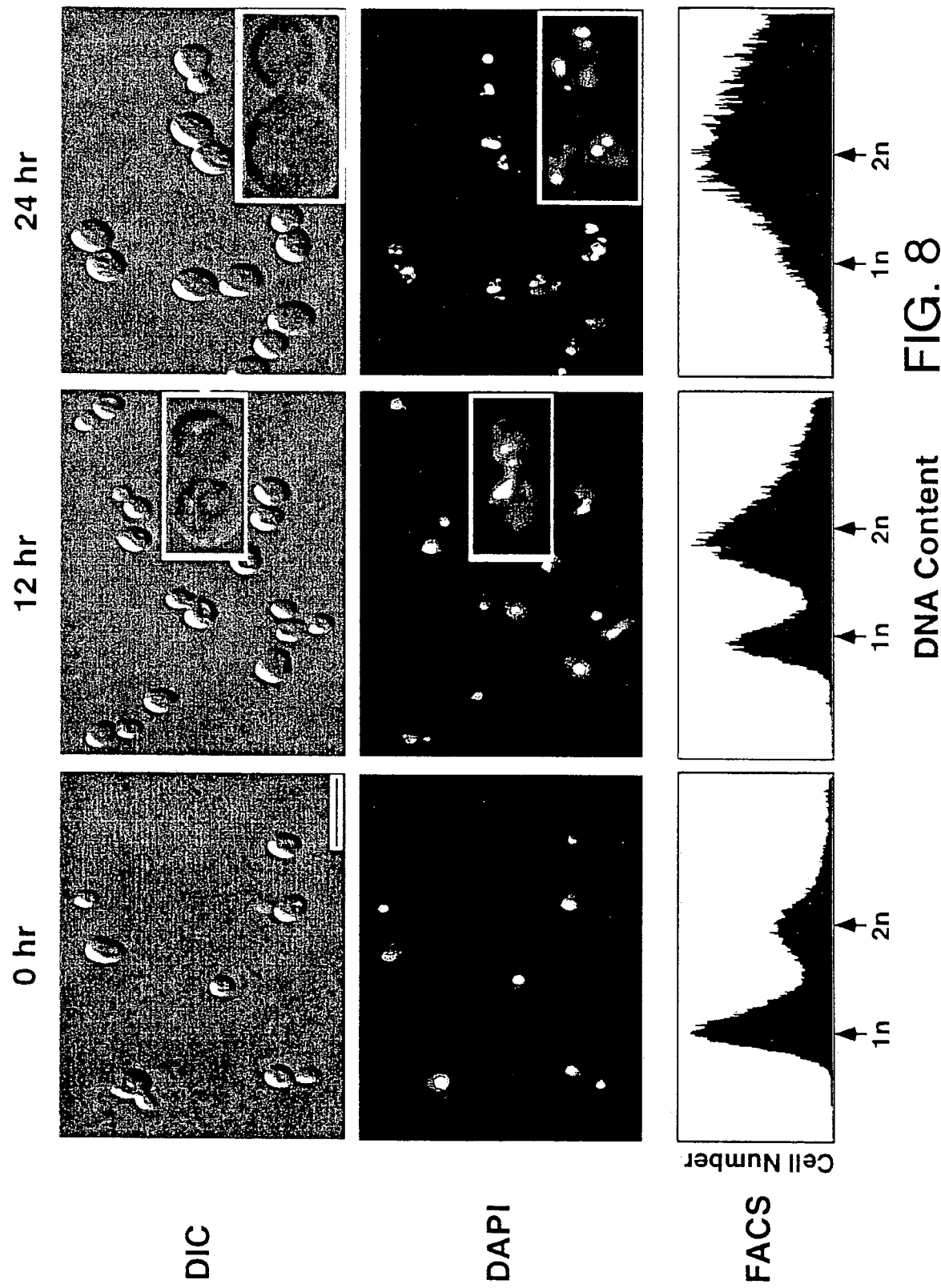
FIG. 8 shows depletion of Pin1/Ess1 results in mitotic arrest and nuclear fragmentation in yeast. A Pin1-dependent strain (YSH12.4) was shifted from inducing media to repressing media, harvested and fixed with 70% ethanol at the times indicated. The cells were stained with DAPI or propidium iodide, followed by videomicroscopy under Nomarksi (DIC) or fluorescent (DAPI) illumination, or FACS analysis, respectively. The bar is 10 μm and the inserts show a higher magnification of a representative cell.

FIG. 8 shows depletion of Pin1/Ess1 results in mitotic arrest and nuclear fragmentation in yeast. A Pin1-dependent strain (YSH12.4) was shifted from inducing media to repressing media, harvested and fixed with 70% ethanol at the times indicated. The cells were stained with DAPI or propidium iodide, followed by videomicroscopy under Nomarksi (DIC) or fluorescent (DAPI) illumination, or FACS analysis, respectively. The bar is 10 μm and the inserts show a higher magnification of a representative cell.

Cells depleted of Pin1 following the shift to repressing media displayed a striking terminal phenotype indicating mitotic arrest (Table 2, FIG. 8). Following about 6 hr of normal growth, cell division was inhibited and by 12 hr, cells began to accumulate in mitosis as judged by the increasing percentage of cells containing a large bud (dumb-bell shape) and by FACS analysis (Table 2, FIG. 8, middle panels). As revealed by DAPI staining, a high percentage of cells containing nuclear staining material in the neck between the mother and the bud, suggesting that mitotic chromosome segregation was slowed or inhibited. Control strains that carried GAL::PIN1, but were wild-type for ESS1, showed normal distribution of cells throughout the cell cycle as judged microscopically and by FACS analysis. By 24 hr., cell division stopped and most cells were arrested in mitosis. Interestingly, cells depleted of Pin1 for extended periods of time (18–30 hr) showed multiple nuclear fragments, which appeared randomly distributed throughout the cell (FIG. 8, right panels). FACS analysis revealed that cells with a 2 n DNA content accumulated over time, with most cells containing 2 n DNA content by 24 hr after the shift to repressing media (FIG. 8, bottom panels). When cells were shifted from noninducing media for expressing media, this phenotypes appeared earlier. Cells were arrested at mitosis by 12 hr with a mitotic chromatin located in the neck in about 40% of cells and nuclear fragmentation in most other cells, indicating the dependence of the phenotypes on the initial level of Pin1 expression. These results show that depletion of Pin1 results in mitotic arrest and eventually nuclear fragmentation; phenotypes similar to those observed in *Aspergillus* and HeLa cells that overproduce NIMA (Osmain et al., *Cell,* 53:237, 1988; O'Connell et al., *EMBO J.,* 13:4926, 1994; Lu and Hunter, *Cell,* 81, 413, 1995a).

TABLE 2

Depletion of Pin1/ESS1 Results in Mitotic Arrest in Budding Yeast

| Time after Shift (hr) | % Unbudded (G1) | % Small Bud (S) | % Medium Bud (G2) | % Large Bud (M) |
| --- | --- | --- | --- | --- |
| 0 | 39.2 | 21.2 | 18.6 | 21.0 |
| 6 | 27.2 | 22.2 | 24.8 | 26.0 |
| 12 | 32.2 | 10.2 | 14.4 | 43.2 |
| 18 | 26.0 | 6.8 | 9.0 | 58.2 |
| 24 | 20.2 | 3.6 | 7.4 | 68.8 |
| 30 | 17.6 | 3.8 | 4.8 | 73.8 |

A Pin1-dependent strain (YSH 12.4) was shifted from inducing media to repressing media, harvested and fixed with ethanol at the times indicated. Bud size distribution was scored under Nomarski illumination after cells were stained with DAP1 and sonicated. About 500 cells were counted for each point.

SUMMARY

Using the yeast two-hybrid system, the present invention identifies the first NIMA-interacting protein of human origin Pin1. Pin1 contains an N-terminal WW domain and a C-terminal PPIase domain, and has PPIase activity in vitro. PIN1 functionally rescues a knockout mutation of the ESS1 gene, which is essential for the growth of budding yeast cells. These results indicate that Pin1 is conserved from yeast to human; Pin1/Ess1 is the first PPIase knows to be essential for life. Pin1 interacts with the C-terminal non-catalytic domain of NIMA and colocalizes with NIMA in a defined nuclear substructure in HeLa cells. Whereas over-expression of Pin1 induces a specific G2 arrest, and delays NIMA-induced mitosis in HeLa cells, depletion of Pin1/Ess1 triggers mitotic arrest and nuclear fragmentation in budding yeast. These results indicate that Pin1 regulates entry into mitosis, probably via the NIMA mitotic pathway.

The primary structure of Pin1 contains two identifiable domains. The C-terminal two-thirds of Pin1 contains residues that are highly conserved in the newly delineated family of PPIases that includes parvulin, PrsA, SurA, NifM, PrtM, Cbf2 and Ess1 (Rudd, et al., *TIBS,* 20:12, 1995). PrsA, SurA, NifM, PrtM have been shown to be involved in maturation and/or transport of specific proteins or protein classes. Parvulin, orininally identified during a chromatographic purification procedure, is the prototype of this family, it contains 96 amino acids and catalyzes the cis/trans isomerization of X-Pro peptide bonds, even in the presence of immunosuppressive drugs (Rahfeld et al., *FEBS Lett.,* 352:180, 1994a and *FEBS Lett.,* 343:65, 1994b). The homology between Pin1 and parvulin spans almost the entire parvulin molecule, strongly sugaesting that Pin1 is a PPIase. The in vitro PPIase assay shown in the above Examples confirms that Pin1 can indeed catalyze the cis/trans isomerization of peptidyl-prolyl peptide bonds.

Although the invention has been described with reference to the presently preferred embodiments, it should be understood that various modifications can be made without deporting from the spirit of the invention. Accordingly, the invention is limited only by the following claims.

What is claimed is:

1. An isolated nucleic acid molecule fragment of a encoding Pin 1 polypeptide consisting of amino acids 5–43 of SEQ ID NO:2 or a functional fragment thereof that binds to NIMA, or a complement of the encoding nucleic acid molecule.

2. The isolated nucleic acid molecule of claim 1 encoding amino acids 5–43 of SEQ ID NO:2 or the complement thereof.

3. The isolated nucleic acid molecule of claim 1 consisting of nucleotides 13–129 of SEQ ID NO:1.

4. An isolated nucleic acid molecule fragment of a encoding Pin 1 polypeptide consisting of amino acids 59–163 of SEQ ID NO:2 or a functional fragment thereof having peptidyl prolyl isomerase activity, or a complement of the nucleic acid molecule.

5. The isolated nucleic acid molecule of claim 4 encoding amino acids 59–163 of SEQ ID NO:2 or the complement thereof.

6. An isolated nucleic acid molecule encoding a fragment of a Pin 1 polypeptide, which Pin 1 polypeptide consists of amino acid residue 1–163 of SEQ ID NO:2, wherein the encoded fragment comprises amino acid residues 5–43 of SEQ ID NO:2 and binds to NIMA.

7. An isolated nucleic acid molecule encoding a fragment of a Pin 1 polypeptide, which Pin 1 polypeptide consists of amino acid residue 1–163 of SEQ ID NO:2, wherein the encoded fragment comprises amino acid residues 59–163 of SEQ ID NO:2 and has peptidyl prolyl isomerase activity.

8. A vector comprising the isolated nucleic acid molecule of claim 1, 4, 6, or 7.

9. An isolated host cell comprising the vector of claim 8.

* * * * *